United States Patent
Guire et al.

(10) Patent No.: US 7,361,724 B2
(45) Date of Patent: Apr. 22, 2008

(54) SELF ASSEMBLING MONOLAYER COMPOSITIONS

(75) Inventors: Patrick E. Guire, Eden Prairie, MN (US); Kristin S. Taton, Little Canada, MN (US)

(73) Assignee: SurModics, Inc., Eden Prairie, MN (US)

( * ) Notice: Subject to any disclaimer, the term of this patent is extended or adjusted under 35 U.S.C. 154(b) by 284 days.

(21) Appl. No.: 10/759,853

(22) Filed: Jan. 15, 2004

(65) Prior Publication Data

US 2004/0146715 A1 Jul. 29, 2004

Related U.S. Application Data

(63) Continuation of application No. 10/163,012, filed on Jun. 4, 2002, now Pat. No. 6,689,473, which is a continuation of application No. 09/907,303, filed on Jul. 17, 2001, now Pat. No. 6,444,318.

(51) Int. Cl.
C08G 64/00 (2006.01)

(52) U.S. Cl. .................. 528/196; 428/333; 428/338; 428/412; 428/423; 528/198; 623/11.11; 623/23; 623/57

(58) Field of Classification Search .......... 428/333, 428/338, 412, 423; 623/23, 57, 11.11; 528/196, 528/198

See application file for complete search history.

(56) References Cited

U.S. PATENT DOCUMENTS

| | | | |
|---|---|---|---|
| 5,258,041 A | 11/1993 | Guire et al. | 435/181 |
| 5,263,992 A | 11/1993 | Guire | 623/66 |
| 5,512,474 A | 4/1996 | Clapper et al. | 435/402 |
| 5,563,056 A | 10/1996 | Swan et al. | 435/180 |
| 5,637,460 A | 6/1997 | Swan et al. | 435/6 |
| 5,741,551 A | 4/1998 | Guire et al. | 427/407.1 |
| 5,744,515 A | 4/1998 | Clapper | 523/113 |
| 5,783,502 A | 7/1998 | Swanson | 442/123 |
| 5,830,539 A | 11/1998 | Yan et al. | 427/551 |
| 5,942,555 A | 8/1999 | Swanson et al. | 522/35 |
| 5,970,381 A | 10/1999 | Ohno et al. | 438/758 |
| 6,077,698 A | 6/2000 | Swan et al. | 435/174 |
| 6,090,995 A | 7/2000 | Reich et al. | 623/11 |
| 6,121,027 A | 9/2000 | Clapper et al. | 435/180 |
| 6,146,767 A | 11/2000 | Schwartz | 428/457 |
| 6,156,345 A | 12/2000 | Chudzik et al. | 424/484 |
| 6,406,921 B1 | 6/2002 | Wagner et al. | |
| 6,444,318 B1 * | 9/2002 | Guire et al. | 428/412 |
| 6,468,649 B1 * | 10/2002 | Zhong | 428/341 |
| 6,497,729 B1 | 12/2002 | Moussy et al. | 623/23.57 |
| 6,630,358 B1 | 10/2003 | Wagner et al. | |
| 6,632,536 B2 | 10/2003 | Buchwalter et al. | |
| 6,838,382 B1 | 1/2005 | Meikle | |

FOREIGN PATENT DOCUMENTS

| | | |
|---|---|---|
| DE | 19827900 | 4/1999 |
| WO | WO 95/12420 | 5/1995 |
| WO | WO 97/16544 | 5/1997 |
| WO | WO 99/16907 | 9/1999 |
| WO | WO 99/43688 | 9/1999 |
| WO | WO 99/47176 | 9/1999 |
| WO | WO 99/55396 | 11/1999 |
| WO | WO 99/64086 | 12/1999 |
| WO | WO 00/40593 | 7/2000 |
| WO | WO 00/44939 | 8/2000 |
| WO | WO 01/21326 | 3/2001 |
| WO | WO 01/23962 | 4/2001 |
| WO | WO 01/44174 | 8/2001 |
| WO | WO 01/66161 | 9/2001 |

OTHER PUBLICATIONS

Noble et al. "Biomaterials Tutorial" Drug Delivery Systems; McAllister, D.V. see abstract.*
Santini, J.T. Jr. , Cima, M.J. & Langer, R. A controlled-release microchip. Nature 397, 335-338 (1999) see abstract.*
McAllister, D.V. , Allen, M.G. & Prausnitz, M.R. Microfabricated microneedles for gene and drug delivery. Annu. Rev. Biomed. Eng. 2, 289-313 (2000) see abstract.*
Shen W. et al., Biomacromolecules 2:70-79 (Dec. 2000).
Gove, Philip Babcock, Ph.D., "Webster's Third New International Dictionary of the English Language Unabridged", p. 1462, G.&C. Merriam Company, Publishers, Springfield, MA.
Whitesides, George M., et al., "Self-Assembly at All Scales", Science, Mar. 29, 2002, pp. 2418-2421, vol. 295, No. 5564, Cambridge, MA.

(Continued)

*Primary Examiner*—Terressa Boykin

(57) ABSTRACT

A surface coating composition for providing a self-assembling monolayer, in stable form, on a material surface or at a suitable interface, as well as a method of preparing such a composition and a method of using such a composition to coat a surface, such as the surface of an implantable medical device, in order to provide the surface with desirable properties. The method provides the covalent attachment of a SAM to a surface in a manner that substantially retains or improves the characteristics and/or performance of both the SAM and the surface itself. Covalent attachment is accomplished by the use of one or more latent reactive groups, e.g., provided by either the surface and/or by the SAM-forming molecules themselves.

23 Claims, 9 Drawing Sheets

OTHER PUBLICATIONS

Lloyd, Douglas R., "Materials Science of Synthetic Membranes", ACS Symposium Series 269, p. 251, 187th Meeting of American Chemical Society, St. Louis, MO, Apr. 9-11, 1984.

Adamson, Arthur W., "Physical Chemistry of Surfaces", Third Edition, pp. 99-103, Dept. of Chemistry, University of S. California, Los Angeles, 1976.

* cited by examiner

SELF ASSEMBLING MONOLAYER COMPOSITIONS

CROSS REFERENCE TO RELATED APPLICATIONS

The present application is a continuation of US patent application filed Jun. 4, 2002 and assigned Ser. No. 10/163,012 now U.S. Pat. No. 6,689,473. including the amendment to the Specification filed on Aug. 19, 2002, which is a continuation of US patent application filed Jul. 17, 2001 and assigned Ser. No. 09/907,303 now U.S. Pat. No. 6,444,318, the entire disclosure of which is incorporated herein by reference.

GOVERNMENT RIGHTS

The government may have certain rights to this invention pursuant to NIH Grant Nos. 1R43 GM58342-01 and 1R43 DK52756, and NSF Grant Nos. DMI96-61439 and DMI99-01713.

TECHNICAL FIELD

In one aspect, the invention relates to methods and materials for passivating the surfaces of implantable devices such as sensors. In another aspect, the present invention relates to self-assembling monolayers, and in particular to the use of such compositions as surface coatings for devices such as implantable medical devices. In yet another aspect, the invention relates to the use of photochemically reactive groups for surface treatment.

BACKGROUND OF THE INVENTION

Materials used to fabricate implantable medical devices, such as implantable biosensors, are generally chosen for their bulk physical properties rather than specific surface characteristics. As a result, while the device may have desirable properties such as strength and elasticity, its surface is typically not optimized for interactions with bodily fluids. Commercially available methods and materials for the surface modification of such devices can be used, for instance, to decrease protein adsorption, increase wettability and lubricity, and decrease thrombus formation and bacterial colonization. However, conventional coating techniques and reagents are frequently not well designed for applications which require ultra-thin coatings.

Such "ultra-thin" applications include those surfaces that provide either small pore sizes or structural features of less than about one micron in size. For instance, biosensors based on solid-phase receptor-ligand assays, such as dot microarray systems, are based on the ability of macromolecules to orient themselves in a desired manner when associated with a substrate surface such as glass. In principal, the properties of the surface itself (e.g., surface charge and/or dipole moment) should be complementary to those of the macromolecule. Experience indicates, however, that most binding proteins are not sufficiently compatible with glass or other surfaces used for the fabrication of biosensors.

Binding molecules, such as coupling molecules or moieties (e.g., N-oxysuccinimide, epoxy groups) or biomolecules (such as biotin/avidin, or biological polymers) can, however, be chemically bonded to surfaces via chemical spacers that hold the binding molecules away from what might otherwise be a harsh environment at the substrate surfaces. In one such embodiment, a hydrophilic surface environment is provided in which protein is attached to intermediate and/or end sites of a bound soluble polymer. It has been suggested that this approach may provide enhanced protein mobility and hence greater opportunities for favorable interaction of the bound capture moiety with its complementary partner. The greatest potential for improving the effectiveness of biochemically-modified surfaces appears to reside in the engineering of surfaces which can immobilize proteins via reactive spacer arms containing specific-binding ligands. Ideally, the base material should stabilize the binding protein and should minimize non-specific interactions.

Various attempts have been made to provide passivated, biomolecule-compatible synthetic surfaces. These attempts have included the design and production of improved plastics, as well as the use of the thin-film coatings of plastic, silica, semiconductor, and metal surfaces. Significant progress on the latter approach has been reported from several academic, government, and industrial laboratories. Such studies have tended to rely upon the adsorption and thermochemical bonding of preformed hydrophilic and surfactant polymers, in situ polymerization/crosslinking to form hydrophilic but insoluble polymeric films, or photochemical bonding of preformed hydrophilic and surfactant polymers.

None of these approaches, however, seem to have achieved an optimal combination of such properties as: 1) complete and uniform surface coverage with an ultrathin film, 2) a hydrophilic surface having minimum nonspecific attraction for biomolecules and cells, 3) sufficient stability for use as the surface of an implantable medical surface, 4) broad applicability to various plastic and inorganic sensor and medical device materials, and/or 5) ease and reproducibility of the coating process. Moreover, the passivated surface should be easily formed by conventional manufacturing processes and be resistant to those conventional sterilization techniques that implants undergo before surgical implantation.

On a separate subject, self-assembled monolayer ("SAM") technology has been used to generate monomolecular films of biological and non-biological (e.g., synthetic polymeric) molecules on a variety of substrates. The formation of such monolayer systems is versatile and can provide a method for the in vitro development of bio-surfaces which are able to mimic naturally occurring molecular recognition processes. SAMs also permit reliable control over the packing density and the environment of an immobilized recognition center or multiple center, at a substrate surface.

Generally, SAMs remain upon a given surface by virtue of various noncovalent interactions between the two. Applicants are aware of at least one example, however, in which polymer-supported lipid bilayers were attached to a substrate that had been functionalized with benzophenone. See Shen W. et al., Biomacromolecules 2:70-79 (December, 2000). As an aside, and with regard to the attachment of proteins using benzophenone derivatized surfaces, see also Dorman and Prestwich, TIBTECH 18:64 (2000) which reviews the use of benzophenone groups on proteins and on surfaces for biomolecule immobilization.

On yet another subject, the assignee of the present invention has previously described a variety of applications for the use of photochemistry, and in particular, photoreactive groups, e.g., for attaching polymers and other molecules to support surfaces. See, for instance, U.S. Pat. Nos. 4,722,906, 4,826,759, 4,973,493, 4,979,959, 5,002,582, 5,073,484, 5,217,492, 5,258,041, 5,263,992, 5,414,075, 5,512,329, 5,512,474, 5,563,056, 5,637,460, 5,654,162, 5,707,818, 5,714,360, 5,741,551, 5,744,515, 5,783,502, 5,858,653, 5,942,555, 5,981,298, 6,007,833, 6,020,147, 6,077,698, 6,090,995, 6,121,027, 6,156,345, 6,214,901 and published PCT Application Nos. US82/06148, US87/01018, US87/02675, US88/04487, US88/04491, US89/02914, US90/05028, US90/06554, US93/01248, US93/10523, US94/12659, US95/16333, US96/07695, US96/08797, US96/17645, US97/05344, US98/16605, US98/20140, US99/03862, US99/05244, US99/05245, US99/08310, US99/12533, US99/21247, US00/00535, US00/01944, US00/33643 and unpublished PCT Application No. US01/40255.

What is clearly needed are methods and reagents for providing improved surface coatings, including those having further improved combination of the various desirable properties listed above.

SUMMARY OF THE INVENTION

The present invention provides a surface coating composition for providing a surfactant monolayer, such as self-assembling monolayer ("SAM"), in stable form, on a material surface or at a suitable interface. The invention further provides a method of preparing such a composition and a method of using such a composition to coat a surface, such as the surface of an implantable medical device, in order to provide the surface with desirable properties. In alternative embodiments, the invention provides material surfaces coated with, or adapted (e.g., primed) to be coated with, such a composition, and articles fabricated from such materials, as well as methods of making and using such material surfaces and resultant articles.

The term "self assembling monolayer", as used herein, will generally refer to any suitable composition, typically surfactant composition, sufficient to form a substantial monolayer upon a particular surface under the conditions of use. The surfactant can itself be of a single type, or domain, but is preferably of a type that includes two ("diblock"), three ("tri-block") or more discrete domains of distinct polarities that correspond with the surface and carrier solvent, respectively. By "substantially monolayer" it is meant that the molecules can form a substantially complete layer covering the surface (or desired portions thereof), ideally positioning the molecules within covalent binding proximity of the surface itself. Such a monolayer does not preclude, and in fact facilitates, the preparation and use of additional "layers" of either the same and/or different molecules.

In one aspect, the invention provides the covalent attachment of a SAM to a surface in a manner that substantially retains or improves the characteristics and/or performance of both the SAM and the surface itself. Covalent attachment is accomplished by the use of one or more latent reactive groups, e.g., provided by either the surface and/or by the SAM-forming molecules themselves. SAM-forming molecules that are themselves derivatized with photoreactive groups, as described herein, are considered to be novel in their own right. In an optional embodiment, the invention provides the stable (though not necessarily covalent) attachment of a SAM to a surface, by either the polymerization of SAM-forming molecules (e.g., that themselves provide polymerizable groups) in the form of a film upon the surface, and/or by the formation of intermolecular bonds between the self-assembling monolayer molecules formed upon the surface, via activation of the latent reactive groups. In addition to either, or both, forms of stable film formation, the invention includes the additional option of covalent attachment to the surface itself, via activation of the same or different latent reactive groups.

Surfaces coated with SAMs, according to this invention, can be used for a variety of purposes, including as passivating surfaces, and/or for the immobilization of binding molecules (e.g., biomolecules) onto the surface, as well as for new or improved physical-chemical properties such as lubricity. The method of this invention can be used to directly attach SAMs to a variety of material surfaces, particularly including most polymeric surfaces (e.g., plastics). Suitable surfaces can include, for instance, flat or shaped (e.g., molded) surfaces, such as those provided by chips, sheets, beads, microtiter wells, either used alone or in combination with other materials or devices. The method provides particular advantages, in terms of its ease of use, and low cost, coupled with the ability to provide complete, uniform coatings.

Such surfaces have particular utility for use as the surface of implantable biosensors, in order to provide a desired passivating effect. By "passivating", as used herein, it is meant that the surface is sufficiently protected against the undesired, nonspecific attachment of compounds or cells during use within the body. In turn, the biosensor can be used for its desired purpose of the specific attachment of corresponding molecules to the particular binding molecules provided on the surface.

Such surfaces also have particular utility for the preparation of insertable "emboli capturing" devices for use in capturing emboli within a body lumen. Such devices typically include an expandable mesh or web-like emboli capturing device mounted on an elongate member and movable between a radially expanded position and a radially contracted position. When in the expanded position, the emboli capturing device forms a basket with a proximally opening mouth.

Optionally, and particularly where the surfaces are not themselves amenable to reaction with photoreactive groups, a suitable intermediate coating can be applied to provide latent reactive (e.g., photoreactive) groups to the surface itself. For instance, with ceramic or glass surfaces, a photoreactive silane can be prepared or obtained in the manner described herein and applied. Similarly, with surfaces of gold or other noble metals, an intermediate layer can be provided using a photoreactive sulfur compound (e.g., thiol or thioether such as methyl thioxanthone) or other suitable compound, as described herein. In yet another optional, and preferred, embodiment, a SAM can be formed at a suitable interface, and optionally transferred to a solid support surface.

DETAILED DESCRIPTION

Figure 1:
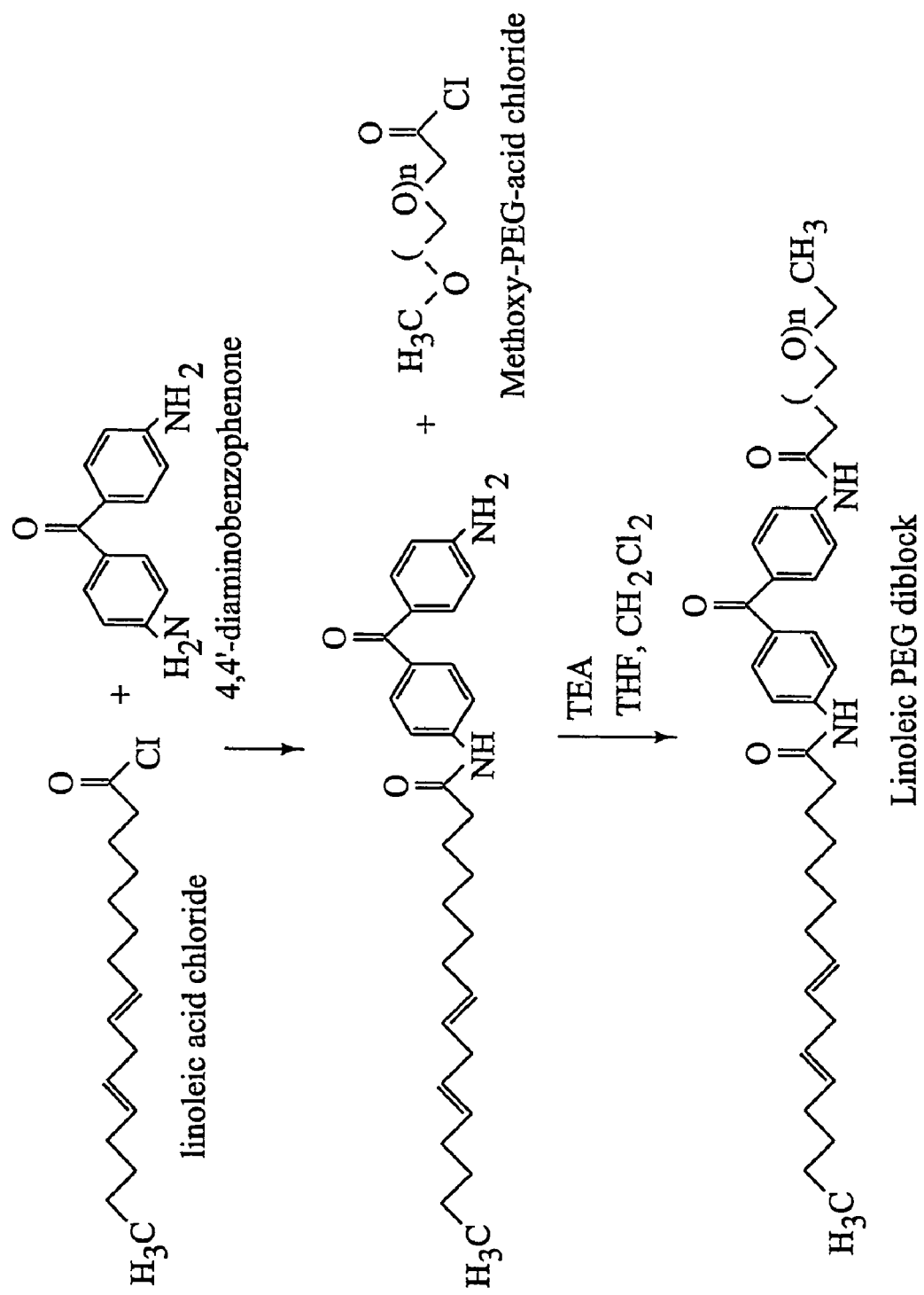
FIG. 1 shows the synthesis of linoleamide PEG (where TEA=triethylamine).

The present invention provides a method for forming a self-assembling monolayer on a surface, the method comprising the steps of: a) providing on the surface both latent reactive groups and a monolayer formed of self-assembling monolayer molecules, and b) activating the latent reactive groups under conditions suitable to either covalently attach the self-assembled monolayer to the surface and/or to form a stable monolayer film on the surface, either by initiating polymerization of suitable groups provided by self-assembling monolayer molecules themselves and/or by forming intermolecular bonds between the self-assembling monolayer molecules. In one preferred embodiment, the latent reactive groups are photoreactive aryl ketones and are provided by the surface itself, while in another, the SAM-forming molecules have themselves been provided with photoreactive aryl ketones.

More preferably, the self-assembling monolayer molecules comprise amphiphilic molecules comprised of either: a) a hydrophobic domain which spontaneously associates with the surface from a polar solvent, and of a hydrophilic domain which allows the molecules to be dispersed in the polar solvent and which remains associated with the polar phase after monolayer formation on the surface, or b) a hydrophilic domain which spontaneously associates with the surface from a nonpolar solvent, and of a hydrophobic domain which allows the molecules to be dispersed in a nonpolar solvent and which remains associated with the nonpolar phase after monolayer formation on the surface.

The method can be adapted for use with any suitable surface, e.g., substantially flat or molded surfaces. The surface, in turn, can be provided by a material selected from ceramics, metals and polymeric materials. For instance, the surface can be provided by a material selected from organosilane-pretreated glasses, organosilane-pretreated silicon materials, and silicon hydrides, or by a polymeric material selected from the group consisting of polystyrene, polycarbonate, polyester, polyethylene, polyethylene terephthalate (PET), polyglycolic acid (PGA), polyolefin, poly-(p-phenyleneterephthalamide), polyphosphazene, polypropylene, polytetrafluoroethylene, polyurethane, polyvinyl chloride, polyacrylate (including polymethacrylate), and silicone elastomers, as well as copolymers and combinations thereof.

In an optional embodiment, the surface can be coated with an intermediate coating adapted to provide latent reactive groups to the surface, for instance, wherein the surface comprises a ceramic, silicon oxide, metal oxide, or glass surface, and the intermediate layer comprises a photoreactive silane.

In another optional embodiment, the self-assembling monolayer molecules themselves provide thermochemical reactive groups and the method comprises the further step of attaching binding molecules to the monolayer by reaction between corresponding reactive groups of the binding molecules and the reactive groups of the self-assembling monolayer molecules. Such molecules can be used in a method that includes the further steps of:

a) providing binding molecules having one or more corresponding thermochemical reactive groups and attaching the binding molecules to the self-assembling monolayer molecules via thermochemical interactions between their respective thermochemical reactive groups, and b) coating the surface with the monolayer in order to provide an immobilized SAM having the binding molecules attached thereto.

Preferably, the binding molecules are selected from the group consisting of coupling molecules and biological polymers, and the binding molecules are attached to the self-assembling monolayer molecules prior to coating and immobilizing the self-assembling monolayer.

Applicants have discovered the manner in which latent reactive chemistry can be used, in combination with the formation of self assembling monolayers, to provide improved coatings. Applicants have found, for instance, that various physico-chemical properties (e.g., surfactancy) of the SAM itself can be retained (and optionally improved) and used to establish desired molecular interactions at interfaces or upon surfaces.

The term "SAM composition", as used with respect to the present invention, will generally refer to a composition containing surfactant (preferably amphiphilic SAM-forming) molecules provided in a carrier phase (e.g., carrier solvent). The composition can, in turn, be brought into sufficient proximity to a suitable surface or interface (e.g., liquid-liquid, liquid-air or liquid-solid interface), to permit the molecules to spontaneously orient themselves into substantially monolayer form upon the surface or at the interface. By "amphiphilic" it is meant that the molecules have two or more functional (and generally discrete) domains, each with corresponding and differing physical properties. In a preferred embodiment, those properties are in the form of differing affinities for water, e.g., water-soluble and water-insoluble groups. In turn, one or more first domains will have an increased affinity (e.g., hydrophobic nature) for the surface or interface, while one or more second domains have an increased affinity (e.g., hydrophilic nature) for the carrier solvent.

The carrier solvent (in which the SAM-forming molecules are initially provided) and the support surface (to which the carrier solvent is applied), will themselves typically have different affinities for water, corresponding to the respective domains of the SAM. In turn, when a composition of SAM molecules in carrier solvent is brought into physical proximity with the surface, or interface, the molecule domains spontaneously and preferentially orient themselves toward either the solvent or surface/interface, in order to form a monolayer. The carrier solvent, in turn, is ideally one in which the second domain of the SAM-forming molecule has preferential solubility or affinity, and which itself is not a solvent for the surface.

During and/or upon formation of the monolayer, the latent reactive groups, which are provided by either the surface (or at the interface with another phase) and/or the SAM-forming molecules themselves, can be activated in order to covalently attach the thus-formed monolayer to the surface or interface. The present invention is therefore not limited by the choice of SAM composition, or by the choice of surface/interface, but instead provides a means that is generally applicable for covalently attaching the formed monolayer to the corresponding surface or at the corresponding interface.

The method and composition of the present invention address and respond to the desire to provide a stable film upon a surface, preferably in the form of an intact, complete cover. An optimal combination of properties can be provided, including for instance, surfactancy, free-radical crosslinking, and photochemical diradical coupling. In turn, the invention provides a composition adapted to spontaneously form a monolayer which: 1) substantially completely covers the hydrophobic surface (at least covering if not displacing such mobile "flaws" on the surface as plasticizers and particles), 2) converts through free-radical crosslinking from a weak non-covalent association to a covalent, substantially monolayer film, and 3) covalently bonds the polymerized (and intermolecularly crosslinked) monolayer film to the underlying surface.

In a preferred embodiment the method and composition are adapted for use with substantially flat or molded surfaces, such as those provided by organosilane-pretreated glass, organosilane-pretreated silicon, silicon hydride, or plastic (e.g., polymethylmethacrylate, polystyrene, polycarbonate, polyethylene, or polypropylene). In another embodiment, the method and composition are used to immobilize SAMs onto plastic materials such as microwell plates, e.g., for use in hybridization assays.

Support surfaces can be prepared from a variety of materials, including but not limited to plastic materials selected from the group consisting of crystalline thermoplastics (e.g., high and low density polyethylenes, polypropylenes, acetal resins, nylons and thermoplastic polyesters) and amorphous thermoplastics (e.g., polycarbonates and poly(methyl methacrylates). Suitable plastic or glass materials provide a desired combination of such properties as rigidity, surface uniformity, resistance to long term deformation, and resistance to thermal degradation.

Examples of suitable support materials include metals, minerals or ceramics, and polymers. Suitable metals include reactive metals, such as, for example, aluminum, chromium, cobalt, iron, tantalum, titanium, and alloys thereof, as well as nitinol and other nickel-titanium alloys, and stainless steels. Examples of suitable minerals or ceramics include alumina, hydroxyapatite, quartz, sapphire, silica and glasses.

Other suitable support materials include polymers such as, for example, polystyrene, polycarbonate, polyester, polyethylene, polyethylene terephthalate (PET), polyglycolic acid (PGA), polyolefin, poly-(p-phenyleneterephthalamide), polyphosphazene, polypropylene, polytetrafluoroethylene, polyurethane, polyvinyl chloride, polyacrylate (including polymethacrylate), and silicone elastomers, as well as copolymers and combinations thereof.

The present invention, in turn, provides a method for immobilizing a SAM upon a support surface, the method comprising the steps of:

a) providing both a support having a surface and a SAM composition, either or both of which are provided with suitable latent reactive groups, and b) forming a coating of the composition on the support surface (e.g., by immersing the support in the composition), and covalently attaching the resultant coating to the support surface (e.g., by simultaneously and/or sequentially activating the latent reactive groups).

Optionally, and particularly if the SAM has remaining or other suitable reactive groups, the method can be used to further immobilize biomolecules such as biopolymers, and particularly those selected from nucleic acids, proteins, polysaccharides, in which case the method can include the further steps of: Such biomolecules can also be immobilized simultaneously or sequentially with the formation and attachment of the SAM itself.

In such an optional approach, the method can include the further step of c) providing a biomolecule, such as a biopolymer (e.g., nucleic acid, protein, and/or polysaccharide) having one or more corresponding thermochemical reactive groups (e.g., amine, hydroxyl, or sulfhydryl groups), d) attaching the biomolecule to the combination of SAM and support (e.g., via thermochemical interactions with the thus coated and immobilized SAM), and e) using the resultant support surface for its intended purpose, such as further immobilizing biomolecules reactive with the attached biomolecules. For example, such further biomolecules can include nucleic acids for use in hybridization to corresponding nucleic acids attached to arrays, or in microplate wells.

Such SAM-forming compositions can also be used, for instance, for the spontaneous formation of monolayers at an interface between two immiscible materials. The use of reversibly-activatible arylketone photochemistry provides an optimal coupling efficiency with a broad variety of target materials, by means of a hydrogen abstraction reaction, resulting in the formation of stable carbon-carbon bonds. The composition and method of this invention can be used to provide an optimal combination of latent reactivity with surfactancy and, when desired, with macromer character, to provide a means for coating surfaces with a relatively thin film which stably imparts a desirable new (e.g., passivating) property to the surface.

SAMs of the present inventions can be prepared using various methods, such as the Langmuir Blodgett technique which involves the transfer of a film pre-assembled at an air water interface to a solid substrate. SAMs can also be prepared by a self-assembly process that occurs spontaneously upon immersion of a suitable substrate into a solution containing an appropriate amphiphile.

Of the water-soluble candidate polymers, poly(ethylene oxide) (PEO) is particularly preferred for use as the hydrophilic domain, since it is uncharged, relatively weak in hydrogen bond formation, and flexible enough in the tethered (i.e., covalently attached) state to present a relatively large excluded volume in the aqueous phase at the interface.

Preferred SAM-forming molecules suitable for use in the present invention are available commercially, e.g., as the Pluronics line of surfactants available from BASF Corporation. Such surfactants are provided in the form of block copolymers of ethylene oxide (EO) and propylene oxide (PO). According to BASF literature, most other nonionic surfactant classes limit the number of available hydrophobes and effect changes in surfactant function only by altering the hydrophile. By comparison, PLURONIC and PLURONIC R surfactants allow incremental alteration of both hydrophobe and hydrophile. In addition, heteric or alternating EO/PO structures can be introduced internally or at the end of the molecule. Finally, total molecular weight can be varied.

PLURONIC brand nonionic surfactants are block copolymers of propylene oxide and ethylene oxide. The propylene oxide block is sandwiched between two ethylene oxide blocks (where both x and y can range from about 10 to about 50, independently).

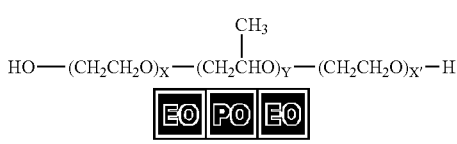

Synthesis of PLURONIC brand surfactants involves a two-step process:
1. Creating a hydrophobe of the desired molecular weight by the controlled addition of propylene oxide to the two hydroxyl groups of propylene glycol.
2. Adding ethylene oxide to sandwich the hydrophobe between hydrophilic groups. The hydrophilic groups constitute from 10% to 80% (by weight) of the final molecule.

Since both the ratio and weights of EO and PO vary within this family of surfactants, information is commercially available by the manufacturers for use in understanding the relationship between copolymer structure, physical form and surfactant characteristics.

The widespread use of PLURONIC surfactants has led to further modifications that provide an even broader selection of surfactant properties and characteristics. Reversing the hydrophobic and hydrophilic blocks of the PLURONIC structure creates the "PLURONIC R" line of surfactants, said to have similar properties, but with some important differences.

$$\text{HO} - (\text{CHCH}_2\text{O})_X - (\text{CH}_2\text{CH}_2\text{O})_Y - (\text{CH}_2\text{CHO})_X - \text{H}$$
$$\quad\quad\;\; |\text{CH}_3 \quad\quad\quad\quad\quad\quad\quad\quad\quad\quad |\text{CH}_3$$

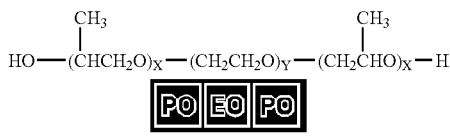

Synthesizing PLURONIC R surfactants is also a two-step process:
1. Creating a hydrophile of the desired molecular weight by the controlled addition of ethylene oxide to ethylene glycol.
2. Adding propylene oxide to create hydrobic blocks on the outside of the molecule.

Similarly, a PLURONIC R grid is available and provides a graphic approach to understanding the relationship between surfactant structure, key physio-chemical properties and function.

Self-assembly, in the manner described herein, provides a means to achieve uniform complete coatings with a minimum of coating material because of the intrinsic attraction between the substrate and the coating material. In addition, it also provides a mechanism for deposition of the thinnest coatings possible—monolayer. Monolayer (or substantially monolayer) self-assembly can be used to create coatings for medical devices and biosensors having surfaces with improved passivation against non-specific protein adsorption and bacterial adherence. Such improvement is due, at least in part, to both the smooth, complete coverage accomplished by the layer itself, and to the improved durability imparted by covalent attachment according to the present invention. Applicants have found that self-assembly promotes the development of thin, uniform and passivating coatings with a minimum of material needed.

Two particularly preferred classes of self-assembling photoreactive polymers were synthesized and are exemplified below, namely, fatty acid PEGs and polyethers. The two classes of compounds are each in the form of a photoreactive diblock molecule, and in turn, each contain a polyethylene glycol (PEG) domain, sufficient to passivate surfaces against protein adsorption, and a hydrophobic domain, sufficient to aid in assembly on the plastic surface. Such PEG diblocks are able to spontaneously self-assemble on hydrophobic surfaces. The other key feature of the exemplified compounds is their photoreactivity; since each contains benzophenone moieties. Once irradiated, the benzophenone exists as a reactive triplet state that can abstract hydrogen atoms from the surface and then combine to form a carbon-carbon bond with the resulting surface radicals. The resulting composition permits one to "fix" the amphiphilic diblock molecules that self-assemble on the plastic by irradiating the molecules upon the surface with ultraviolet light.

Coating a surface through the self-assembly process can be accomplished in a single step and is applicable to most biomaterials. These amphiphilic molecules are comprised of a photoactive hydrophobic domain which spontaneously associates with the surface from an aqueous solution, and of a hydrophilic domain which allows the molecule to be dispersed in water and which remains associated with the aqueous phase after monolayer formation on the surface.

A covalent linkage can thus be achieved between the biomaterial surface and the hydrophobic domain of the copolymer. In turn, the hydrophilic domain remains free and extended into the aqueous solution, presumably causing the biomolecules in solution to effectively "see" only a surface covered with the hydrophilic domain, a opposed to the underlying hydrophobic domain or base material. Therefore the hydrophilic domain ideally present minimum attractive forces to the biomolecule and maximum repulsive forces. Electrostatic forces are both attractive and repulsive to most proteins and cellular materials and hydrogen bonding is an essentially universally attractive force for them, therefore the hydrophilic domain might best be neutral, with minimum hydrogen bonding potential and maximum kinetic repulsion energy.

Reagents of the invention optionally carry one or more pendent latent reactive (preferably photoreactive) groups covalently bonded to the polymer backbone. Alternatively, such photoreactive groups can be provided by the support surface itself, or by suitable linking reagents. Photoreactive groups are defined herein, and preferred groups are sufficiently stable to be stored under conditions in which they retain such properties. See, e.g., U.S. Pat. No. 5,002,582, the disclosure of which is incorporated herein by reference. Latent reactive groups can be chosen that are responsive to various portions of the electromagnetic spectrum, with those responsive to ultraviolet and visible portions of the spectrum (referred to herein as "photoreactive") being particularly preferred.

Photoreactive groups respond to specific applied external stimuli to undergo active specie generation with resultant covalent bonding to an adjacent chemical structure, e.g., as provided by the same or a different molecule. Photoreactive groups are those groups of atoms in a molecule that retain their covalent bonds unchanged under conditions of storage but that, upon activation by an external energy source, form covalent bonds with other molecules.

The photoreactive groups generate active species such as free radicals and particularly nitrenes, carbenes, and excited states of ketones upon absorption of electromagnetic energy. Photoreactive groups may be chosen to be responsive to various portions of the electromagnetic spectrum, and photoreactive groups that are responsive to e.g., ultraviolet and visible portions of the spectrum are preferred and may be referred to herein occasionally as "photochemical group" or "photogroup".

Photoreactive aryl ketones are preferred, such as acetophenone, benzophenone, anthraquinone, anthrone, and anthrone-like heterocycles (i.e., heterocyclic analogs of anthrone such as those having N, O, or S in the 10-position), or their substituted (e.g., ring substituted) derivatives. The functional groups of such ketones are preferred since they are readily capable of undergoing the activation/inactivation/reactivation cycle described herein. Benzophenone is a particularly preferred photoreactive moiety, since it is capable of photochemical excitation with the initial formation of an excited singlet state that undergoes intersystem crossing to the triplet state. The excited triplet state can insert into carbon-hydrogen bonds by abstraction of a hydrogen atom (from a support surface, for example), thus creating a radical pair. Subsequent collapse of the radical pair leads to formation of a new carbon-carbon bond. If a reactive bond (e.g., carbon-hydrogen) is not available for bonding, the ultraviolet light-induced excitation of the benzophenone group is reversible and the molecule returns to ground state energy level upon removal of the energy source. Photoactivatible aryl ketones such as benzophenone and acetophenone are of particular importance inasmuch as these groups are subject to multiple reactivation in water and hence provide increased coating efficiency. Hence, photoreactive aryl ketones are particularly preferred.

The azides constitute a preferred class of photoreactive groups and include arylazides ($C_6R_5N_3$) such as phenyl azide and particularly 4-fluoro-3-nitrophenyl azide, acyl azides (—CO—$N_3$) such as benzoyl azide and p-methylbenzoyl azide, azido formates (—O—CO—$N_3$) such as ethyl azidoformate, phenyl azidoformate, sulfonyl azides (—$SO_2$—$N_3$) such as benzenesulfonyl azide, and phosphoryl azides $(RO)_2PON_3$ such as diphenyl phosphoryl azide and diethyl phosphoryl azide. Diazo compounds constitute another class of photoreactive groups and include diazoalkanes (—$CHN_2$) such as diazomethane and diphenyldiazomethane, diazoketones (—CO—$CHN_2$) such as diazoacetophenone and 1-trifluoromethyl-1-diazo-2-pentanone, diazoacetates (—O—CO—$CHN_2$) such as t-butyl diazoacetate and phenyl diazoacetate, and beta-keto-alpha-diazoacetates (—CO—$CN_2$—CO—O—) such as t-butyl alpha diazoacetoacetate. Other photoreactive groups include the diazirines (—$CHN_2$) such as 3-trifluoromethyl-3-phenyldiazirine, and ketenes (—CH=C=O) such as ketene and diphenylketene.

Upon activation of the photoreactive groups, the reagent molecules are covalently bound to each other and/or to the material surface by covalent bonds through residues of the photoreactive groups. Exemplary photoreactive groups, and their residues upon activation, are shown as follows.

| Photoreactive | Group | Residue Functionality |
|---|---|---|
| aryl azides | amine | R—NH—R' |
| acyl azides | amide | R—CO—NH—R' |
| azidoformates | carbamate | R—O—CO—NH—R' |
| sulfonyl azides | sulfonamide | R—$SO_2$—NH—R' |
| phosphoryl azides | phosphoramide | $(RO)_2PO$—NH—R' |
| diazoalkanes | new C—C bond | |
| diazoketones | new C—C bond and ketone | |
| diazoacetates | new C—C bond and ester | |
| beta-keto-alpha-diazoacetates | new C—C bond and beta-ketoester | |
| aliphatic azo | new C—C bond | |
| diazirines | new C—C bond | |
| ketenes | new C—C bond | |
| photoactivated ketones | new C—C bond and alcohol | |

One or more latent reactive groups can be attached to SAM-forming reagents in any suitable manner. Preferably the latent reactive groups are themselves covalently attached to the reagent, either directly or via linking groups. A coating composition of this invention can be prepared by any suitable means, e.g., by providing a SAM-forming molecule with one or more latent reactive groups, incorporated before or after its preparation. For instance, a complete SAM-forming molecule can be derivatized with one or more latent reactive groups by covalently attaching the latent reactive group either at a reactive or functionalized end of a molecule, or at a reactive or functionalized pendant position. SAM-forming molecules frequently possess hydroxyl, or other reactive functionalities on either end of the molecule. Less frequently, these same functionalities branch off the main polymer backbone and can also be derivatized with latent reactive groups.

By contrast, a SAM-forming molecule can be synthesized in a manner that provides the resultant molecule with one or more latent reactive moieties, for instance, by incorporating such groups into the building blocks used to prepare the SAM-forming molecule itself. For instance, monomers for polymerization can be made which contain photoreactive groups. Provided that polymerization is done without ultraviolet light or using groups that are protected, the photoreactive groups will retain their ability to photofix the self-assembling molecule in place after self-assembly. Alternately the SAM-forming molecule can be synthesized from two or three sections, any of which may contain latent reactive groups, after which the sections can themselves be combined to provide the SAM-forming molecule.

Those skilled in the art, given the present description, will appreciate the manner in which the number, location, and spacing of latent reactive groups can be controlled by the design of the synthesis of the self-assembling molecule. For example, designs that combine two or more sections to create blocks with different hydrophobicities, can employ different building blocks with different amounts of latent reactive groups. Self-assembly requires blocks of differing hydrophobicity or attractiveness to the solvent, however the difference may be slight as in the case of Pluronics brand triblock compounds, where the middle block contains one more carbon in the monomer unit than the outer blocks. Therefore, photoreactive groups can be incorporated into any of the blocks of the SAM-forming molecule. The building blocks can be fabricated by random polymerization of photoreactive and non-photoreactive monomers, whereby controlling the ratio of monomers introduced into the system would control the photoload of the final block synthesized. Alternately, a building block can be fabricated with a specific number of photoreactive groups at designated locations either side by side or located at some distance from one another. By coupling different building blocks, of which at least one but possibly several are photoreactive, different photoreactive SAMs can be created with photoreactive groups on different blocks and in different ratios.

In a preferred embodiment, for instance, photogroups are attached by polymerizing a photoreactive monomer such as benzophenone coupled to an epoxide, acrylate, acrylamide, methacrylate, methacrylamide, styrene, vinyl pyridine, vinyl pyrrolidone, or other suitable monomer. This photoreactive monomer, in turn, can be polymerized in the presence of non-photoreactive monomers of either the same or different types. In a particularly preferred embodiment, polymerization is initiated off of a non-photoreactive block of differing hydrophobicity, thus creating the photoreactive SAM in one step. By comparison, the photoreactive polymer can also be covalently coupled to another block of differing hydrophobicity through a linker or a second block could be polymerized off of the first with different monomers or a different monomer ratio.

In another preferred embodiment, a pre-formed hydrophilic block is coupled through a hydroxyl functionality to another pre-formed block, which is more hydrophobic. This hydrophobic block has been previously derivatized by attaching a benzophenone, or other photoreactive group, on one end. This synthesis can be accomplished in two steps and gives products with very well defined architecture.

The composition and method of the present invention can be used, for instance, to provide monolayer coatings on polymeric materials having small apertures, in a manner that permits those materials to be coated without clogging those apertures. In one such preferred embodiment, for instance, the SAM-forming molecules are themselves derivatized with one or more suitable photogroups. In a particularly preferred embodiment, the one or more first domains (having affinity for a surface or interface) are provided with one or more latent reactive groups covalently bonded thereto. In the course of forming a monolayer, the first domains position themselves in sufficient proximity to a surface (during and/or following formation of the monolayer) to permit the attached latent reactive groups to be activated in order to form a covalent attachment between the SAM and the surface.

The composition and method can also be used to provide monolayer coatings on inorganic substrates such as glass, ceramics and metals such as noble metals. In such embodiments, the surfaces themselves can be derivatized, directly or via intermediate coatings, so as to provide suitable latent reactive groups or suitable hydrophobic targets for coupling with photoreactive groups. The SAM composition, with or without latent reactive groups of its own, can then be coated onto the surface and covalently attached thereto by activation of the latent reactive groups. The present invention provides, for instance, intermediate coating reagents that can be used to coat an inorganic surface to provide the surface with latent reactive groups. In a preferred embodiment, for instance, this intermediate coating reagent comprises a photosilane reagent as described herein. A SAM-forming composition can be applied to the thus-coated surface under conditions suitable to permit the surface-bound latent reactive groups to be activated in order to covalently attach the first domains (having affinity for the surface).

In a particularly preferred embodiment, the method and composition are used to coat the surfaces of devices such as emboli catching (also known as "distal protection") devices, of the type described in U.S. Pat. No. 6,245,089, the disclosure of which is incorporated herein by reference. The composition provides particular advantages by being able to suitably coat the surfaces of the porous materials, and thereby alter their physico-chemical features in a desired, controllable fashion, while not unduly clogging the pores in a manner that would render them unsuitable for their intended purpose.

In an alternative preferred embodiment, the present invention combines, inter alia, photochemical coupling and surface coating technology with optical microsensor device technology utilizing glass and silicon chip sensor surfaces. The resultant combination provides a significant improvement in the cost, ease, and spatial control of the chemical bonding of specific binding molecules onto a sensor surface.

In such an embodiment, the method and composition of this invention address current problems in the development of protein-coated biosensor surfaces, by providing a coating chemistry for glass and other sensor materials that is adapted to: a) reduce nonspecific adsorption of interfering biomolecules onto the sensor surface, b) provide a stabilizing molecular environment for storage and function of the immobilized binding biomolecules, c) provide the immobilized binding biomolecule with optimal freedom to interact with its ligand in the solvent and d) provide a cost-effective immobilization procedure for a biological source material.

The present invention presents an approach, for instance, to resolving a critical and enduring obstacle to developing dependable biosensor systems for the timely measure of multiple markers for gene sequences, cancers, infectious diseases, and toxic agents. The present invention permits, for instance, the development and use of improved multianalyte biosensor technology for health-related microanalyses. The present invention further permits the extension of latent reactive group technology into general passivation of the surface and patterned immobilization of binding groups on the sensor surface.

A typical sensor surface, for instance, is glass passivated with amphiphilic polymers or proteins and patterned with the widely useful biotin—avidin binding pair. Biotin can be (1) covalently bound to the passivated surface photochemically in microdots (e.g., between about 1 micron and about 500 micron average diameter) by illumination through a mask, (2) saturated with its very high affinity, multi-site binding protein X-avidin (avidin, Neutravidin™, or streptavidin) by affinity binding from crude source material, and (3) the immobilized X-avidin dots loaded by ink-jet printing and/or contact printing with the desired biotinylated oligonucleotides for detection/identification. This approach thus presents an innovative combination of diradical photochemistry, self assembly, and high-affinity specific binding pairs to provide a cost-effective coating technology for patterned multianalyte biosensor surfaces.

The modification of surfaces with micro/nano-patterns is a technology which is rapidly expanding in importance to information acquisition, storage, processing, and distribution. Application areas of special interest include: (1) biosensors (especially the bonding and functional interactions of specific-binding biomolecules with sensor surfaces) [1], (2) patterned growth and function of cells on diagnostic and hybrid organ surfaces (e.g., nerve regeneration and functional nerve-electrode connections) [2], and (3) stable deposition/adhesion of conductive circuits on insulator surfaces [3]. Applicants have synthesized and provide improved photoreactive reagents and demonstrate surface coating technology for the micro-patterned bonding of widely applicable biochemical binding agents (e.g., biotin) to glass and silicon wafers for use with optical devices for sensitive, specific, and rapid multi-analyte sensing capabilities.

The composition and method of the present invention provide a commercially-available solution to the need for a cost-effective method for preparing functionally stable specific-binding molecules on biosensor surfaces. This composition and its use are adaptable to the facile immobilization of a wide variety of specific binding proteins, including oligonucleotides and antibodies, onto sensor surfaces made significantly more compatible for biomolecule storage and function by this passivating/stabilizing coating. The provision of a photoactivatible sensor surface and its complete coverage with a covalently bound thin film of passivating hydrophilic polymer [19] containing an array of specific binding groups, can alleviate the problem of weak signal-to-noise ratio resulting from loss of activity of the specific binding protein and from assay interference by non-specific binding of components of the assay sample.

This development of reagents and technology for the passivation of biosensor surfaces and the micropatterned immobilization thereon of specific biochemical binding agents for the analysis of gene sequences, demonstrates the applicability of such coating technology to such uses with biotinylated oligonucleotides and antibodies as:

Infectious disease diagnosis—diagnosis-related groups of viral and microbial pathogens, including antibiotic resistance;

Gene sequencing—an alternative to the photodeprotection combinatorial solid-phase synthetic chemistry utilized by Affymetrix and others [29];

Gene defect assessment—for genetic diseases such as cystic fibrosis, breast cancer, colon cancer, etc.

Parentage assessment/Forensic determinations;

Chemical and biological agent detection and identification;

Drugs of abuse detection and measurement.

In a related fashion, Applicants have found that these, and other, features and characteristics makes this technology particularly suitable for patterned high resolution biomolecule immobilization. By way of example, Applicants have targeted the avidin—biotin high-affinity ($k_a=10^{15}$ M$^{-1}$) general-binding biosensor as a suitable model for development of this unique photochemical surface "tailoring" technology for biosensor applications.

As described herein, the word "passivation" generally refers to the prevention of nonspecific binding of proteins and cellular materials upon or to a surface positioned in an aqueous (and typically biological) environment. In the present invention, surfaces can be passivated by providing and covalently attaching a spontaneously formed monolayer of surfactant molecules onto what is typically an inherently hydrophobic material surface.

Preferred surfactant molecules are amphiphilic molecules that include both a) one or more hydrophobic first domains sufficient to and b) one or more discrete hydrophilic second domains sufficient to permit the molecule to be dispersed in aqueous carrier fluids. When the composition is applied to a hydrophobic surface, the hydrophobic domains spontaneously associate with the surface from the aqueous carrier fluid, forming a monolayer of the molecules, with the hydrophilic domains remaining associated with the aqueous phase. The latent reactive groups, in turn, can be provided by either the hydrophobic domains and/or the surface itself, in a manner that permits the groups to be activated and form a covalent linkage between the hydrophobic portion (and in turn, the reagent itself) and the surface.

The hydrophilic domains, in turn, are free to contact, or interact with, biomolecules in the surrounding environment (e.g., solution and/or tissue contacting the surface). The hydrophilic domains can be selected and used to provide a desired level of attractive or repulsive forces to the biomolecule of choice.

The presently described approach to passivation of surfaces with stable thin films can be used, for instance, with a variety of materials used for biosensors and medical devices, including those formed of such materials as polystyrene, polycarbonate, and polypropylene microwell plates and on glass slides precoated with hexamethyldisilazane (to provide a hydrophobic hydrocarbon-containing surface for surfactant deposition and photochemical coupling).

The composition and method of this invention are also facile, reproducible, and cost-effective in comparison to those currently known to be used or under development. The surface to be coated can simply be exposed in an appropriate manner to an aqueous solution or suspension of the photo-surfactant, rinsed briefly, if necessary, to remove micelles or other excess reagent, and illuminated in the wet condition.

The ability to minimize the binding of protein and cellular structures to solid surfaces is of great commercial value to the medical device industry in general, and to the biosensor industry in particular. The composition and method of this invention have demonstrated improved results with a variety of biosensor and medical device materials, and are particularly well suited to be optimized and developed to the pilot assembly and production assembly scale.

The invention will be further described with reference to the following non-limiting Examples. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments. Unless otherwise indicated, all percentages are by weight and all molecular weights are expressed as the number average.

EXAMPLES

The following Examples are divided into two general categories: 1) latent reactive self-assembling monolayer (SAM) coatings in which the latent reactive group is part of the coating composition, and 2) the use of non-photoreactive self-assembling monolayer coatings on surfaces that themselves provide the latent reactive function. Molecular weights are provided as the number average molecular weight, unless otherwise indicated. The Examples can be outlined as follows:

I. Self-assembling Monolayer Coatings Containing Latent Reactive Groups
   1. Synthesis
      A. Fatty acid-polyethylene glycol (PEG) compounds
         1. Addition of 4,4'-diaminobenzophenone to linoleoyl chloride
         2. Addition of 4-amino,4'-linoleamide-benzophenone to mono-methoxy-polyethyleneglycol-acid chloride
      B. Polyethers
         1. General epoxide polymerization
   2. General coating method for diblock copolymers
   3. Surface analysis
   4. Surface evaluation—passivation levels of optimized coatings II. Self-assembling Monolayer Coatings on a Surface Which Contains Latent Reactive Groups
   1. Preparation of photoreactive glass surface
   2. Creation and passivation of a biosensor surface against non-specific adsorption of biomolecules
   3. Creating biosensors with functionalized SAMs on a photosurface
   4. Using SAMs on a photosurface to create an oligonucleotide microarray of four analytes The present examples describe, inter alia, the synthesis of SAM-forming molecules in the form of copolymers comprising at least one substantially hydrophilic polyethylene glycol (PEG) domain and at least one substantially hydrophobic alkane domain, which have added latent reactive (e.g., photoreactive) groups. When provided within suitable (polar) carrier solvents, these molecules are able to self-assemble on hydrophobic plastics and then be fixed in place by illumination, yielding durable passivating coatings. The optional inclusion of vinyl groups in the hydrophobic domain further allows crosslinking and polymerization of the coating with added monomers, macromers, and/or polymers, if desired. Those skilled in the art, given the present description, will appreciate the manner in which the number and location of photoreactive groups, the type, number and location of polymer groups (e.g., vinyl), and the characteristics of the hydrophilic domain (e.g., length of the PEG backbone) can be independently varied.

Once applied to the surface, self-assembly can occur by the use of aqueous solutions of SAM-forming molecules at very dilute concentrations (on the order of 0.01 mg/ml to 1 mg/ml of carrier solvent) and within 30 minutes. Coatings of this invention can be made extremely thin, ideally as a monolayer, yet durably bound to the surface. Preferred coatings (e.g., having PEG as the hydrophilic domain) offer a passivating effect against non-specific protein adsorption and bacterial adherence.

Two general types of photoreactive SAM-forming compounds are exemplified below. As an example of one type, fatty acid-PEG compounds are synthesized by joining a hydrophilic PEG chain with a hydrophobic fatty acid through a benzophenone molecule. In this case, the benzophenone serves both as a photofixative agent and as a spacer to connect the two disparate parts of the molecule. These compounds can be varied by changing the length of the PEG chain, or by using different fatty acids for the hydrophobic chain. Using this approach, the degree of photoreactivity is generally not changed, since typically only one benzophenone is used per molecule. The second type, photoreactive polyethers, allow better flexibility in design and synthesis of SAMs. This group of diblock polymers is made with a preformed PEG chain serving as the anionic initiator of epoxide polymerization. By varying the number of epoxide monomers used for the polymerization, the photoload, hydrophobicity, and potential for additional crosslinking can be selected and controlled.

Both types of diblock compounds are capable of self-assembly, e.g., onto hydrophobic plastic surfaces from aqueous solutions. Both can be covalently bound to the plastics by irradiation with ultraviolet light, providing a PEG coating on the plastic. Once bound the resultant PEG coatings serve to passivate the plastic against non-specific protein adsorption and bacterial adherence.

Example 1

Synthesis of Fatty Acid-PEG Compounds

Linoleic acid was chosen as a representative fatty acid to describe the synthesis of photoreactive fatty acid-PEG diblocks. The linoleamide PEG compounds synthesized consist of two domains, including a methoxy-terminated PEG domain and a hydrophobic linoleic domain. The overall synthetic scheme to produce linoleamide PEG compounds included the initial attachment of 4,4'-diaminobenzophenone to linoleoyl chloride, followed by the attachment of a PEG compound, suitably functionalized with an acid chloride moiety as seen in FIG. 1. Purification was typically required after the first step, in order to remove undesired products, including unreacted reagents and products in which linoleoyl chloride reacted at both amino positions.

Addition of 4,4'-diaminobenzophenone to linoleoyl chloride

The diaminobenzophenone (0.71 g) was dissolved in dry tetrahydrofuran (THF, 65 ml) in a flame-dried roundbottom flask under a nitrogen atmosphere. Linoleoyl chloride (1 g) was added via syringe from a sealed ampoule. The reaction mixture was stirred at room temperature for one hour, followed by a water quench and purification by extraction and washing. The crude reaction mixture was further purified by column chromatography with 95:5 chloroform-:methanol eluent, in order to yield 0.96 g of a yellow oil.

Addition of 4-amino,4'-linoleamide-benzophenone to mono-methoxy-polyethyleneglycol-acid chloride Mono-methoxy polyethylene glycol acid (1.75 g, MW ~5000, Shearwater Polymers, Huntsville, Ala.) was dissolved in dry methylene chloride and oxalyl chloride (0.5 ml) was added under a nitrogen atmosphere. Bubbling ensued and the reaction mixture was stirred at room temperature overnight. The solvent was removed by rotary evaporation and the PEG-acid chloride was washed two times with chloroform. The PEG acid chloride was then re-dissolved in a 1:1 (v/v) mixture of methylene chloride: tetrahydrofuran under an argon atmosphere. A solution of benzophenone linoleamide (0.15 g) in tetrahydrofuran (10 ml) was added dropwise to reaction mixture followed by triethylamine (0.1 ml). After two hours, the reaction was complete and quenched by the addition of a 10% w/v sodium carbonate aqueous solution. The organic layer was washed again with the sodium carbonate solution, then washed with aqueous HCl (0.1 N), and finally washed with deionized water, before being dried over magnesium sulfate. The product was isolated by column chromatography with 90:10 (v/v) chloroform:methanol as the eluent, in order to provide a final product having a yield of 0.99 g.

Similar procedures synthesized compounds with the polyethylene glycol domains having molecular weights of 750 and 350, respectively.

Synthesis of Polyethers

Figure 2:
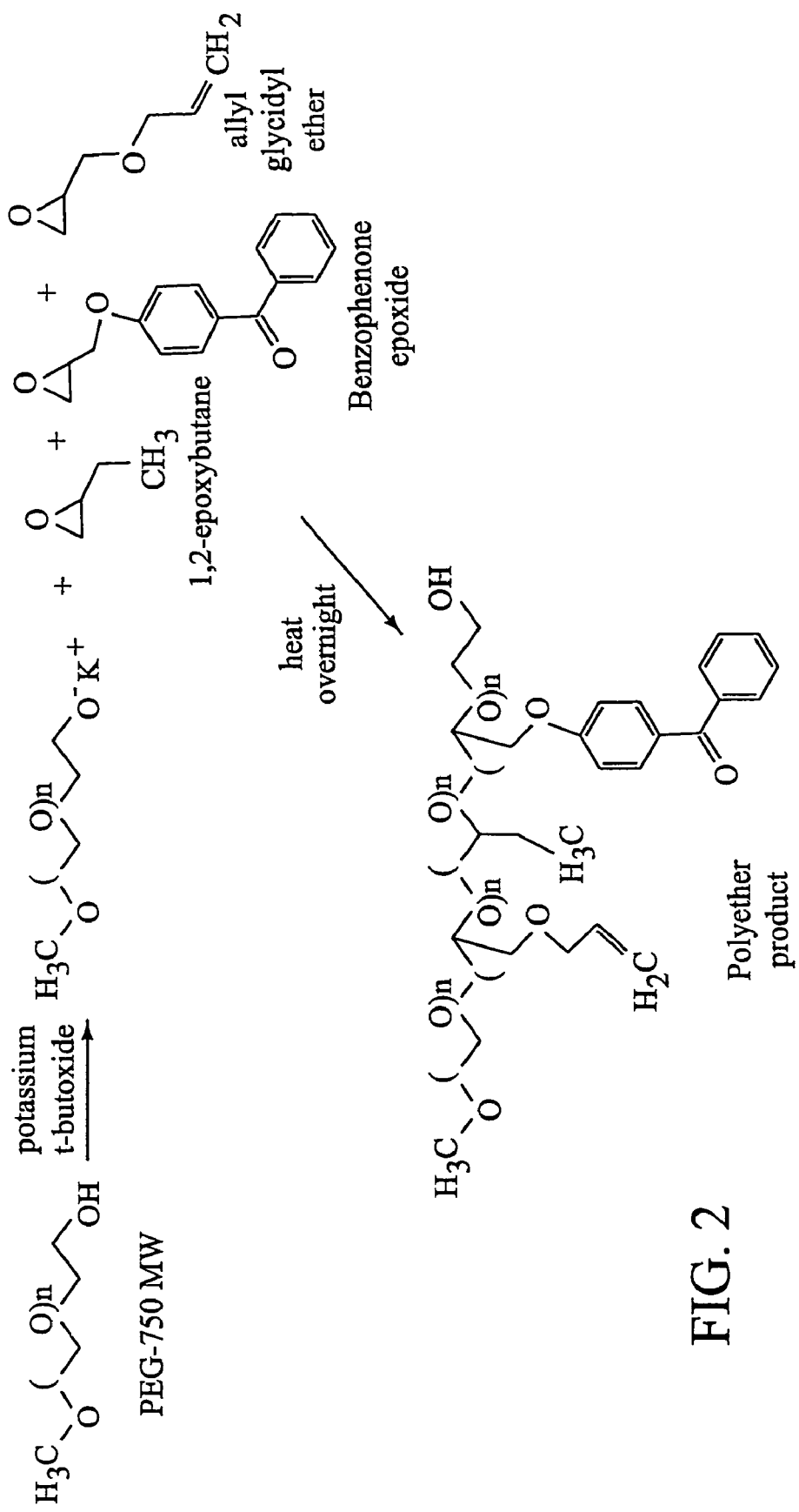
FIG. 2 shows the synthesis of photoreactive polyether.

Polyethers were synthesized by initiating anionic polymerization from a deprotonated pre-formed mono-methoxy PEG and polymerizing a variety of functionalized epoxides as seen in FIG. 2. The epoxides were derivatized with a benzophenone group, an ethyl group, or an allyloxy group. All these groups are significantly more hydrophobic than polyethyleneglycol, thereby forming a diblock with a hydrophilic domain and a hydrophobic domain, similar to PEG-linoleamide.

General Epoxide Polymerization

Mono-methoxy PEG (1.15 g, Shearwater Polymers, 750 MW) and potassium t-butoxide (0.15 g) were mixed, heated to 90 C and stirred for 45 minutes to deprotonate the mono-methoxy PEG. The development of a dark brown color indicated completion of the reaction. Benzophenone epoxide (1.5 g), 1,2-epoxybutane (0.7 ml), and allyl glycidyl ether (0.7 ml) were added and the solution's temperature reduced to 70° C. to react overnight. Subsequently, the reaction mixture was cooled to room temperature. The product was purified by continuous flow dialysis using deionized water and 1000 MW dialysis tubing.

The purity of the resulting polymers was verified before and after dialysis by $^1$H NMR, which indicated complete polymerization. This synthesis allowed the incorporation of different benzophenone and allyl groups, thereby demonstrating the flexibility of this method as compared to the PEG-linoleamide synthesis described herein. Four different polymers were produced, each with a 750 MW PEG arm (approx. 17 units), and having the following molar ratios of benzophenone:ethyl:allyloxy groups: 30:40:30, 15:55:30, 30:20:50, 15:15:70, respectively. Unless otherwise indicated, molar ratios expressed in this manner herein will refer to molar ratios of benzophenone:alkyl:allyloxy substituents on the hydrophobic block of the polyether. After the photoreactive SAM-forming molecules were synthesized, coating methods were created for these compounds.

Example 2

Coating Methodology

Several coating methodologies for the photoreactive SAM coatings were examined, incorporating various aspects of conventional procedures for self-assembling molecules. For instance, irradiation of the coatings in both the wet and dry state was compared. Both approaches provided some evidence of surface modification, but the wet irradiation was typically superior to dry. Presumably, drying the substrate disturbs the monolayer that has formed on the surface. While not intending to be bound by theory, it would appear that the hydrophobic portion originally associated with the surface, at the water-substrate interface, might reverse itself and associate with the more hydrophobic air at the air-substrate interface.

Unless otherwise specified herein, all coatings were performed with a wet irradiation to ensure that the self-assembly remained in place during the photo-fixing process. Solution concentration, temperature, and soak duration were all optimized for the coatings. Finally the various amphiphilic coatings were compared with one another using the optimal conditions. The coatings were applied with the following general method.

General Coating Method: Cleaned plastic pieces were cut into strips and suspended vertically in test-tubes. The test-tubes were filled with coating solution, generally 0.01 mg/ml to 10 mg/ml of polyether SAM or linoleamide-PEG SAM in deionized water. The plastic pieces were allowed to soak for at least 15 minutes prior to irradiation. An iron-doped mercury vapor lamp (Dymax brand) was used to irradiate the strips for eight minutes, while rotating the strips to ensure uniform exposure and complete bonding. After irradiation the strips were washed three times with deionized water, and optionally also washed with methanol.

Irradiated coatings were evaluated by static contact angle and protein adsorption. Static contact angles were measured immediately after surface deposition with a goniometer (Micro Vu model 400), using the mean results of at least three droplets on each surface. For methoxy-PEG coated surfaces the contact angle with water decreased to approximately 55° C. from 70-80° C. for most of the tested plastics.

Protein adsorption was measured by fluorescence. The coated plastic pieces were shaken for 15 minutes within phosphate buffered saline (PBS) solutions containing a desired fluorescent protein (25 mcg/ml) and subsequently incubated at 37° C. for 1 hour. This step was followed by three rinses each with PBS and deionized water. Protein that remained adsorbed to the surface was then dislodged by dissolving each substrate piece in tetrahydrofuran (1 ml). The fluorescence of those tetrahydrofuran solutions was analyzed with a spectrofluorophotometer (Shimadzu RF-1501). The levels of protein adsorbed to coated pieces was compared with uncoated controls, in order to correlate passivation levels of the various coatings and coating procedures. Generally, it was found that lower fluorescent protein adsorption indicated better coating and passivation.

Coating conditions were evaluated under various parameters, including the concentration of photoreactive SAM-forming compound, soak duration time and/or temperature, wash conditions, and substrate material. Under the conditions evaluated, none of these parameters appeared to provide a large difference in the ultimate level of passivation achieved for any particular compound and substrate. For instance, concentrations of SAM-forming compound from as low as 0.01 mg/ml were generally found to achieve equivalent results as 5 mg/ml. This finding, in turn, indicates that devices such as medical devices can be coated using a minimal amount of material, thus providing an improved combination of features, including cost and ease of preparation.

Additionally, soak times as short as five minutes were generally found to provide adequate coatings. Slightly longer soak times gave more reproducible coatings, with smaller standard deviations, but no additional benefit was typically found with soak times beyond 30 minutes. Coatings were compared on various substrates, including polystyrene, polyvinyl chloride, polypropylene and silanized glass. For any particular coating compound, the results did not vary significantly between the substrates. These results are promising as well, in that they demonstrate that the easiest, most cost effective method of coating (short soak time, low concentration) can be used to provide suitable coatings.

Of the various parameters, only the use of irradiation was found to provide a significant effect on the coatings, and in turn, on resultant properties. Without any irradiation, the coatings could be removed with a simple deionized water wash or a more stringent methanol wash. Once irradiated, the coatings were impervious to such wash conditions.

Figure 3:
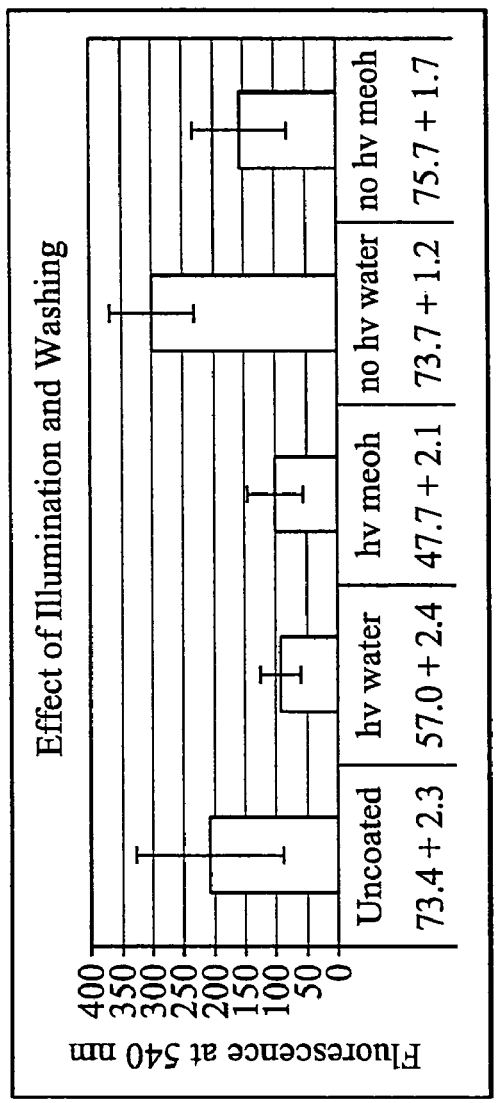
FIG. 3 is a graph showing the effect of illumination and washing on polystyrene pieces coated with polyether 30:40:30, incubated in avidin fluorescently labeled with Oregon Green 488 dye.
Figure 4:
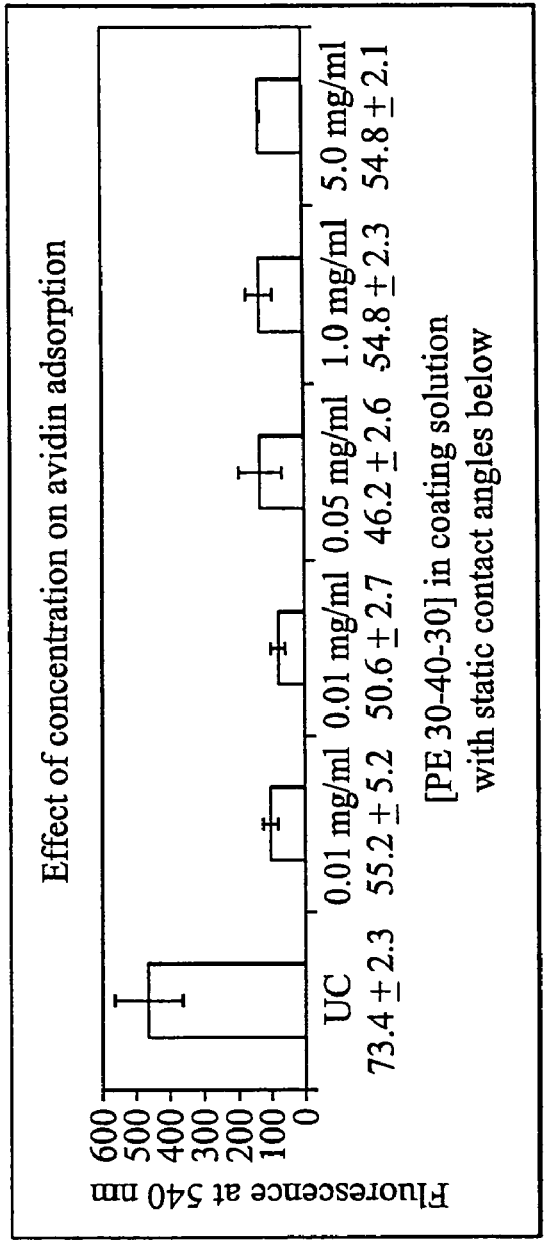
FIG. 4 is a graph showing the effect of concentration on non-specific avidin adsorption on PE 30:40:30 coated polystyrene pieces.
Figure 5:
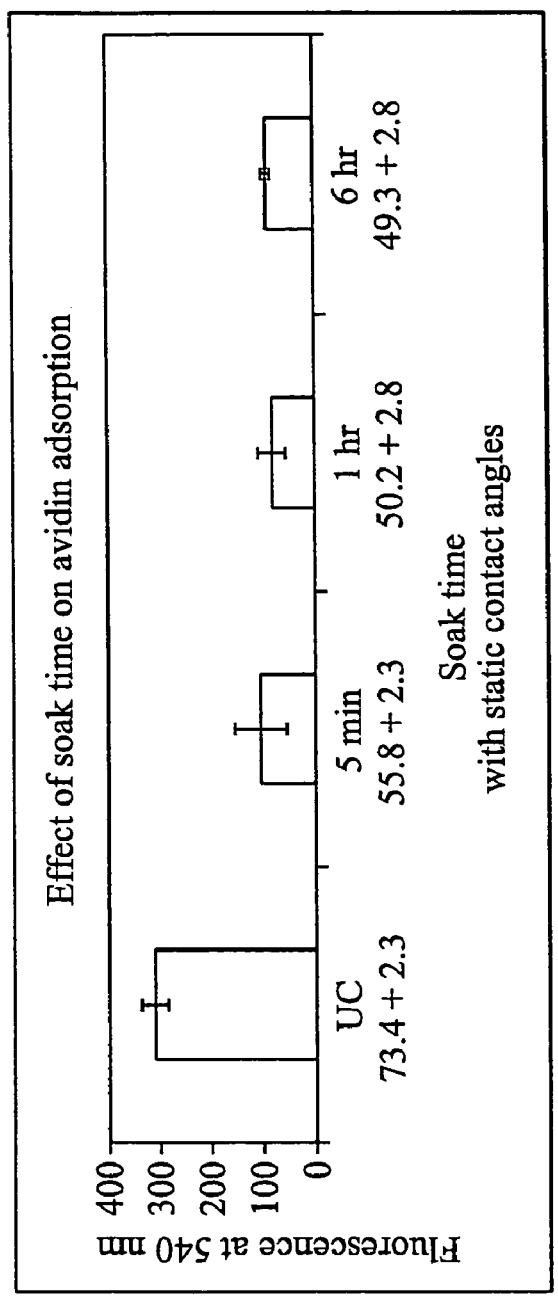
FIG. 5 is a graph showing the effect of soak time on non-specific avidin adsorption on PE 30:40:30 coated polystyrene pieces.
Figure 6:
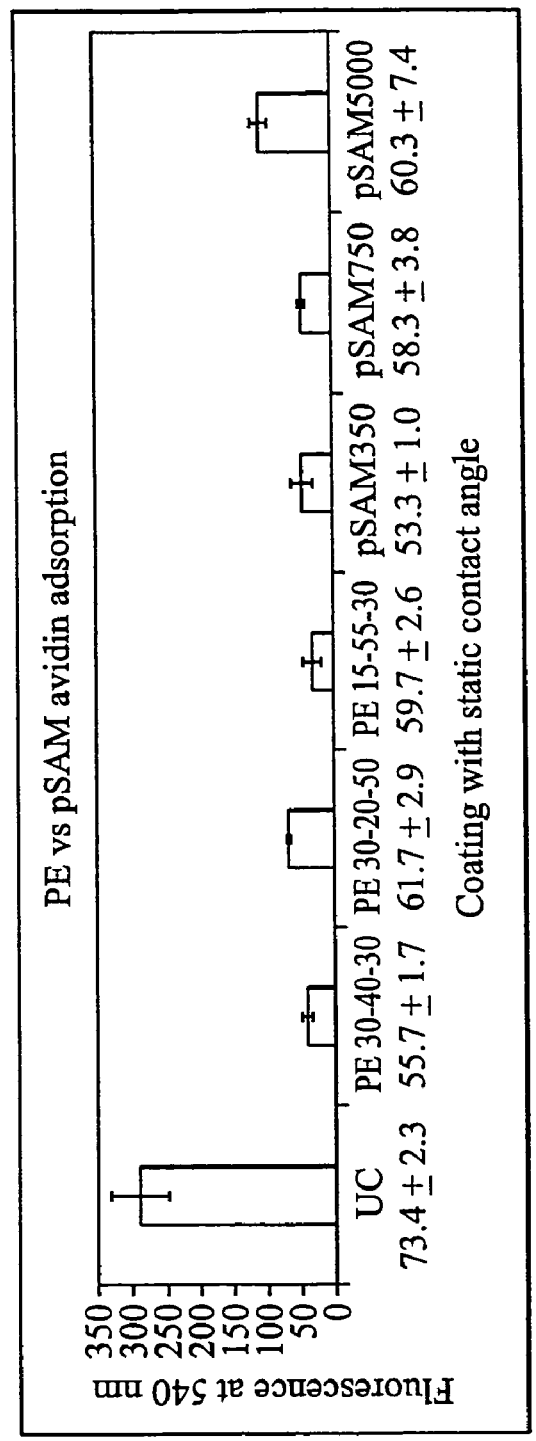
FIG. 6 is a graph comparing the avidin absorption of various polyether ("PE") and linoleamide PEGs synthesized.

All conditions were optimized for polyether (30:40:30) coatings on polystyrene as seen in FIGS. 3, 4, and 5. FIG. 3 shows the effect of illumination and washing on polystyrene pieces coated with polyether 30:40:30, incubated in avidin fluorescently labeled with Oregon Green 488 dye. Water rinses were sufficient to strip away all non-illuminated polyether. (where hv indicates irradiation by UV light and meoh=methanol). Once the optimal conditions were established, the various polyethers and linoleamide-PEG compounds were compared together as seen in FIG. 6. In FIG. 6, the numerical portions of pSAM 350, 750 and 5000 indicate the respective molecular weights of the PEG arms of the diblock molecules. Polyethers (PE) 30:40:30 and 15:55:30 performed the best, however, there was not a large difference between any of the coatings. There appears to be a lot of flexibility in the design of photoreactive diblock compounds for surface passivation.

Surface Analysis

Figure 7:
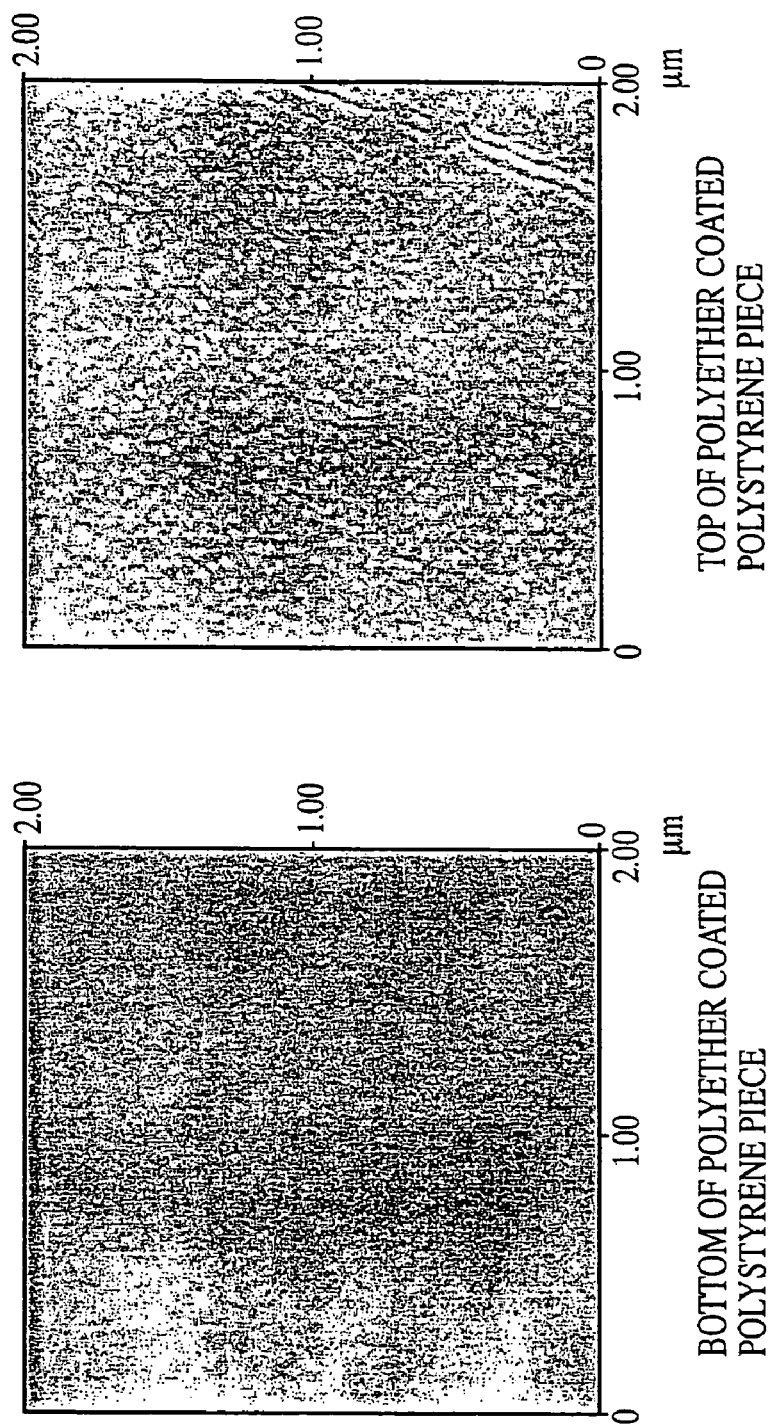
FIG. 7 illustrates diblock copolymer assembly on a surface as revealed by atomic force microscopy.

Surface analysis has provided a better understanding of the coating. AFM has shown the coating to be ultrathin and reasonably uniform. TOF-SIMS gave definite proof that the diblock polymer was present on the surfaces and that the coatings were less than two monolayers thick. Additionally, the AFM analysis showed evidence that the diblock copolymer self-assembles into micelle-like structures in solution or at the solid-liquid interface a seen in FIG. 7. The right side of the figure (Top) shows PE 30-40-30 coated horizontally on polystyrene. The left side of FIG. 7 shows the bottom side of same piece. On the bottom, no micelle-like structures deposited from solution, but the surface has an identical contact angle with water, indicating it is also coated. Pieces coated vertically look much like the bottom picture. All of this information is consistent with the design of the diblock copolymers and bodes well for their further improvement and applications.

AFM measurements were taken using Digital Instruments Nanoscope III in tapping mode, and phase measurements are shown below. For the standard coating method, AFM measurements showed uniform coverage to the extent that there were no large features present. While coated pieces showed lower contact angles with water and lowered protein adsorption, indicating success, the different coatings could not be distinguished.

TOF-SIMS provided a means of detecting the coating and allowed a qualitative understanding of the thickness as well. TOF-SIMS provided mass spectrometric data on the top 1-2 monolayers of a sample of polyether 30:40:30 coated pieces of polystyrene. All TOF-SIMS work was conducted on a Physical Electronics Trift II TOF-SIMS using a 15 kV indium ion source, the sample was analyzed on a raster with a 150 µm×150 µm area with a sample size of 2 µm. TOF-SIMS showed masses associated with the PEG domain of the coating (m/z 45, 89, 133), and the hydrophobic domain from the benzophenone moiety (m/z 77, 105), as well as the allyloxy moiety (m/z 41, 57, 71) and ethyl moiety (m/z 29, 43), collectively verifying that the coating was on the pieces as expected. Additionally, the TOF-SIMS showed evidence of significant polystyrene in the top 1-2 monolayers (m/z 77, 91, 103, 105, 115, 128, 141, 193) indicating that the polyether coating must be extraordinarily thin, and likely less than two monolayers. It is likely that TOF-SIMS analysis demonstrates a slightly thinner coating than may actually arise in solution, because the TOF-SIMS is conducted under vacuum, thus drying down the coating. In turn, the TOF-SIMS data suggests that the present invention does indeed provide monolayer coverage of the surface. This conclusion correlates well with the lack of detectability by AFM, for if visible by AFM, the coating would have had to be considerably thicker.

Surface analysis has provided a better understanding of the coating. AFM has shown the coating to be ultrathin and reasonably uniform. TOF-SIMS gave definite proof that the diblock polymer was present on the surfaces and that the coatings were less than two monolayers thick. Additionally, the AFM analysis showed evidence that the diblock copolymer self-assembles into micelle-like structures in solution or at the solid-liquid interface a seen in FIG. 7. All of this information is consistent with the design of the diblock copolymers and bodes well for their further improvement and applications.

Comparative Example 1

Surface Evaluation: Passivation Levels of Optimized Coatings

Surfaces coated with photoreactive self-assembling molecules can be designed to present important properties, such as passivation against non-specific protein adsorption or bacterial adherence. Using the above methodology for creating photoreactive SAMS, an optimal, formed of 0.1 mg/ml PE 30:40:30 on polystyrene soaked for 30 minutes, was evaluated for protein passivation and bacterial adherence. Three proteins were used to study passivation: fibrinogen, IgG, and avidin. Non-specific adsorption of these proteins was compared for uncoated, polyether 30:40:30 coating and two commercial coatings based on polyacrylamide (PA) and polyvinylpyrrolidone (PVP).

Figure 8:
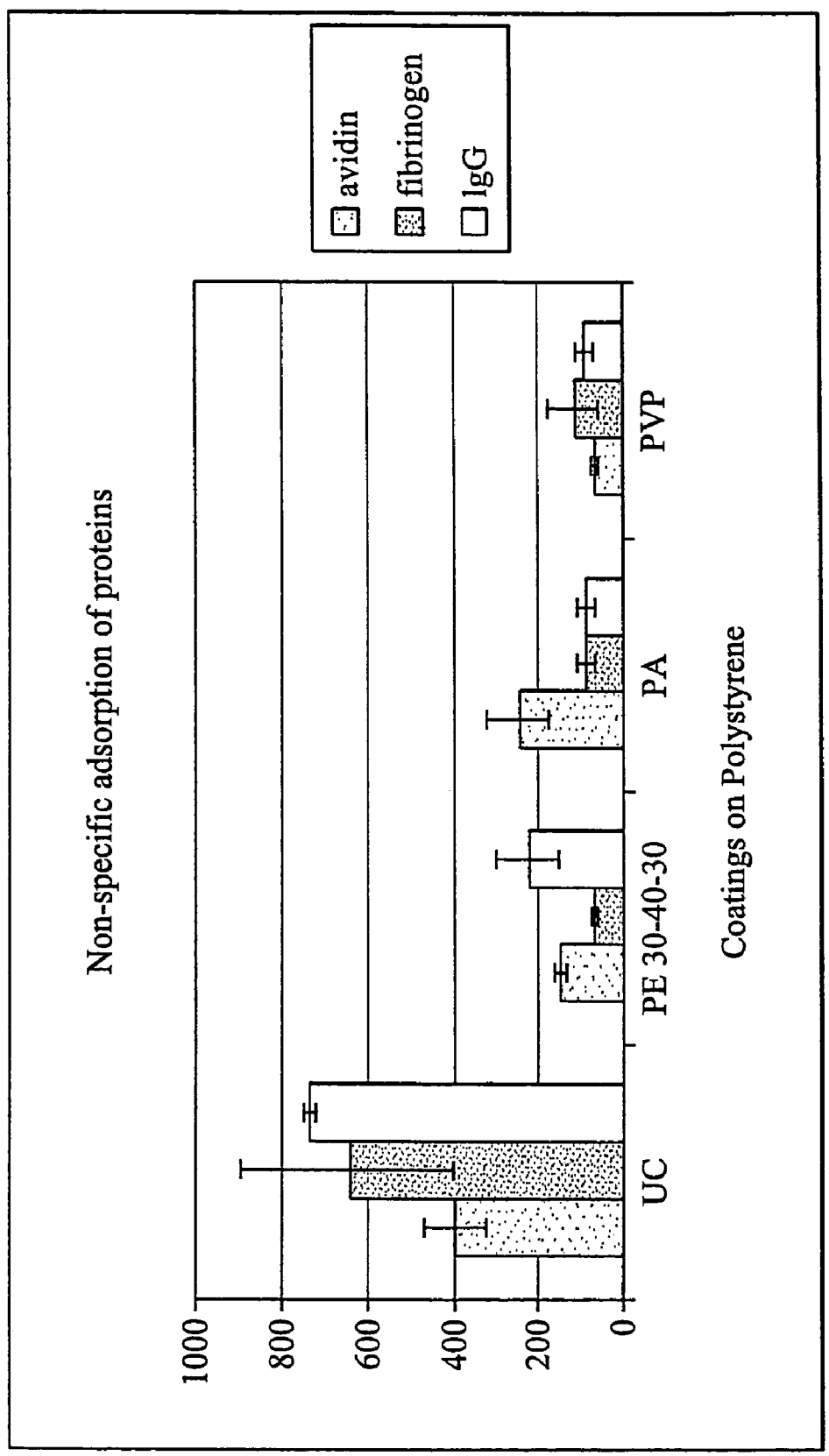
FIG. 8 is a graph comparing different proteins for nonspecific avidin adsorption on PE (30:40:40) coated polystyrene pieces.

The polyether coating passivated as well as PA and PVP against fibrinogen, better than PA but worse than PVP against avidin, and poorer than both PA and PVP against IgG as seen in FIG. 8. Additionally, the fibrinogen results as stated took place under simulated use conditions with an initial 3 day period of shaking in salt solution prior to adsorption of protein to ensure that the coating was robust. Results were comparable to fibrinogen adsorption without simulated use conditions.

Figure 9:
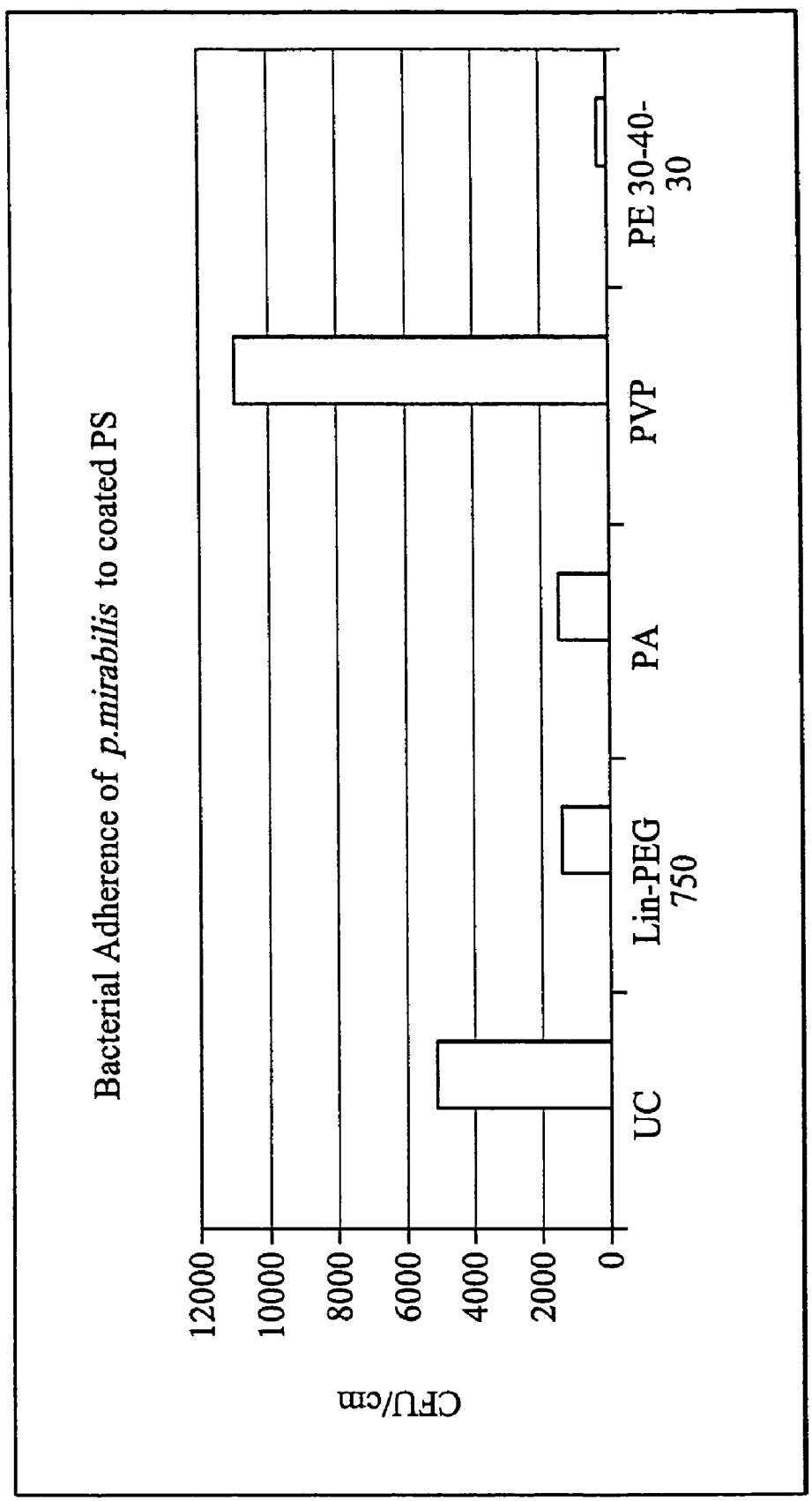
FIG. 9 is a graph evaluating bacterial adherence on PE (30:40:40) coated polystyrene pieces.

Bacterial adherence to polyether coated polystyrene was examined by incubating cleaned coated pieces of polystyrene in a solution of $1\times10^8$ CFU/ml *P. mirabilis* (ATC #15565) in phosphate buffered saline for two hours, then rinsed with additional phosphate buffered saline overnight. The pieces were sonicated in three cycles to remove the bacterial colonies, and the resulting solution was plated onto tryptic soy agar plates and incubated overnight at 37° C. Counting the colonies gave good data on bacterial adherence. The polyether coating was far superior to present commercial PA and PVP coatings, as seen in FIG. 9, reducing bacterial adherence to less than 5% of uncoated polystyrene results.

The polyether coatings reduced protein adsorption 89-70% and bacterial adherence 95.5% versus uncoated samples. This shows significant improvement over uncoated samples and similar results to commercial coatings while using the desirable ultrathin coating methodology. The applicants believe there are numerous commercial applications that can only be accomplished with such a thin coating, and the photoreactive diblock copolymer approach will prove very useful to this niche market.

The previous examples have all been of the type of coating that contains a photoreactive functionality in the self-assembling monolayer. Connecting PEG groups to fatty acids with benzophenones illustrated useful coatings to prevent adherence of protein and bacteria. The following descriptions will portray an alternative embodiment of this invention, namely, the use of self-assembling monolayers on photoreactive surfaces.

Example 3

Preparation and Characterization of Photoreactive Glass Surface

The following two methods are described to exemplify the preparation of photoreactive glass surfaces by applying a photosilane reagent (pSil) or a photoreactive polystyrene derivative (pPS). Both of these methods produced surfaces that could covalently bond self-assembling molecules in the presence of ultraviolet (UV) light.

Figure 10:
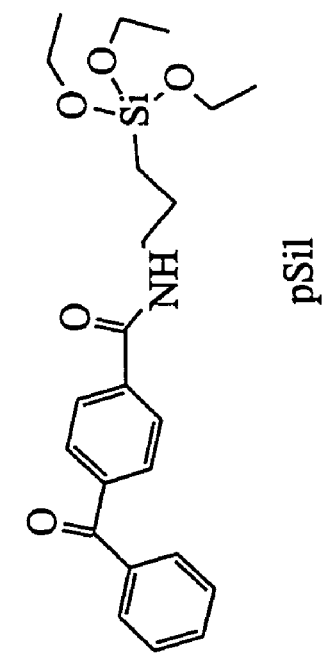
FIG. 10 shows the synthesis of photosilane reagent, pSil.
Figure 10:
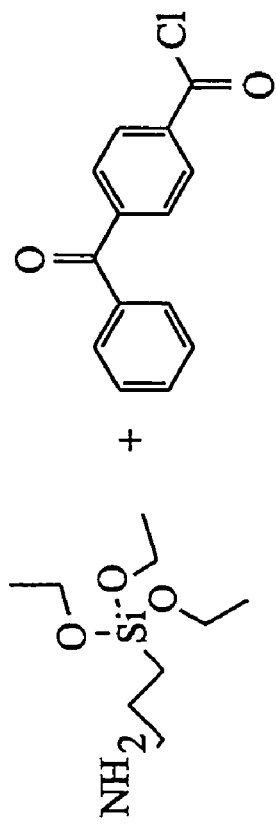

The photosilane molecule was synthesized so that the silane moiety could covalently bond directly to the glass surface. After UV exposure, this would allow a photogroup, benzophenone, to abstract hydrogen atoms and bond molecules to the top of the silane surface. The photosilane was synthesized by adding 3-aminopropyltriethoxysilane to benzoylbenzoic acid chloride in the presence of triethylamine (Et3N) in tetrahydrofuran to create pSil as seen in FIG. 10. Photosilane was filtered then analyzed by thin layer chromatography (TLC), nuclear magnetic resonance spectroscopy (NMR) and Fourier Transform Infrared Spectroscopy (FTIR) to establish purity. Good laboratory methods were used to ensure the dryness of the material. The photoactive surface was generally coated immediately following its production.

This pSil reagent was used to coat cleaned glass slides by soaking in a solution of 1% pSil in 95:5:0.011 ethanol:water: acetic acid for 30 minutes, rinsed with ethanol once, then heated to 100° C. for 30 minutes to remove excess water and ethanol. Static contact angles with water of approximately 60° were common for these pSil surfaces, as compared to uncoated glass contact angles of <30°. These surfaces were examind by TappingMode™ Atomic Force Microscopy (AFM), which indicated complete coverage of the glass surface. Furthermore, an assay based on adsorption of fluorescent avidin which will be described later confirmed the results. The coatings were durable against scratching and solvent rinsing.

In an alternative approach, a photopolymer having an excess of photogroups was used, to permit the polymer to be irradiated twice, once to crosslink the molecules to each other, and again to bond the molecules to the surface. Both the pPS and pSil surfaces can be used as photosurfaces, and both can bond an additional layer of molecules when exposed to ultraviolet light. Photo-polystyrene was synthesized through Friedel-Crafts acylation with benzoyl chloride of polystyrene and aluminum chloride in carbon sulfide. Ultraviolet-analysis showed 90% acylation of the starting polystyrene. This photo-polystyrene (pPS) can be dissolved in toluene. Glass slides with and without an initial layer of n-decyl silane were hand-dipped in a 1% v/v pPS solution in toluene, then irradiated for two minutes with a Dymax iron-doped mercury vapor lamp. These surfaces had static contact angles with water of approximately 70°, indicating good coverage of the glass. Fluorescent avidin assays showed that the pPS surface can covalently bind passivating compounds with efficacy equal to pSil. Making a photoreactive surface with pPS or pSil gave a dependable base to adhere SAMs.

Example 4

Creation and Passivation of a Biosensor Surface Against Non-specific Adsorption of Biomolecules One of the most valuable uses for coatings from self-assembling molecules onto photoreactive surfaces is preventing the non-specific adsorption of biomolecules, or passivation. Non-specific adsorption of biomolecules onto plastics or other substrates can interfere with the ability of an implanted sensor to detect the desired biomolecules, either through increased background signal or by direct interference at the coupling site.

Covalent binding of passivating molecules upon exposure to uv light provided a means of testing both the binding ability of the photosurfaces as well as the passivating ability of the molecules. An assay was developed to test the non-specific adsorption of avidin and DNA to the photosurfaces. The experimental surfaces were submerged for 45 minutes at 37° C. under humid conditions in a solution of fluorescent avidin or DNA in phosphate buffer. After 45 minutes, the slides were rinsed three times with a phosphate buffer solution and three times with deionized water. The slides were then analyzed with the General Scanning ScanArray 3000 fluorescence scanner that returns a picture of the fluorescence on the surface. Low fluorescence indicates low protein adsorption or passivation of the surface.

Several different self-assembling compounds were examined as passivating agents from the triblock copolymer family of poly(ethylene oxide)-poly(butylene oxide)-poly (ethylene oxide) (PEO-PBO-PEO) with differing molecular weights and compositions (Dow Polyglycols). They could be covalently bound (stringent isopropyl alcohol IPA rinses could not dislodge the triblocks) and they passivated well against both avidin and DNA as seen in Table 1. The concentration and composition of the triblock copolymer was optimized. Best conditions were found when irradiating slides in a solution of B20-5000 (Dow Polyglycol) at 5 mg/ml in deionized water, then washing with threefold isopropanol rinses.

TABLE 1

Passivation of coatings against fluorescent protein and oligonucleotides.

| Substrate | Fluorescent oligo adsorption | Fluorescent avidin adsorption |
| --- | --- | --- |
| Uncoated glass | 3575 ± 1311 | 978 ± 333 |
| pSil | 2229 ± 672 | 28847 ± 2144 |
| pSil + triblock | 191 ± 20 | 981 ± 359 |
| PPS | 5645 ± 782 | 29314 ± 1577 |
| PPS + triblock | 3143 ± 365 | 326 ± 32 |

Adsorption of a fluorescent 30-mer DNA strand on triblock-passivated pSil surfaces was decreased by approximately 95% compared to the signal intensity of uncoated glass. Both photosurfaces bound enough triblock copolymer to minimize non-specific avidin binding. Contact angles with water decreased from 60° for pSil or 70° for pPS to 55° with triblock copolymer immobilized on the surface. Both the avidin assay and the surface contact angles showed that the photosurfaces covalently bound triblock copolymers as well as passivated the surfaces against DNA and protein.

Example 5

Creating Biosensors with Functionalized SAMs on a Photosurface

By using a functionalized self-assembling molecule to bind to the photosurface, a new functional group can be introduced onto the surface. Applicants used this approach with a biotinylated triblock copolymer on a photosurface as described above. The biotin spacer derivative that was chosen for use was TriBlock 40-2500 (Dow Polyglycol) that has been biotinylated (TB-b). This reagent was chosen for its ability to passivate the photoglass surface while binding avidin. Patterned immobilization was accomplished using a one-step printing technique onto an initial layer of uniform TB-b deposited with a Mayer Rod. The rod used was designed to create a wet coating that is 0.0007 inches (17.8 μm). A solution of TB-b (3 mg/ml) was coated onto the slides and air dried. The slides were then irradiated and washed in both water and isopropyl alcohol. The extended wash in alcohol will remove any TB-b that is not photoimmobilized onto the surface. This provides a complete, uniform biotin surface that is now ready for avidin immobilization.

Avidin (1 mg/ml) was coupled in carbonate bicarbonate (0.1M, CBC) buffer for ten minutes at room temperature in humid conditions. Slides were then washed with both CBC (0.1M) buffer and deionized water to remove uncoupled avidin prior to printing biotin oligo. Avidin was immobilized to the surface based on its biotin binding capabilities. Radiolabeling experiments were used to examine the amount of streptavidin (SA) bound to the surface and the activity of this SA to bind biotin for further steps. The surface yields 2.43±0.106 pmol/cm$^2$ of SA and 1.180±0.141 pmol/cm$^2$ of biotin-binding capacity on the surface. A secondary method was examined in which avidin is directly photocoupled to the surface without the use of biotin binding. The avidin that was photocoupled to the surface was probably denatured during the photolysis, as avidin does appear to be on the surface ($2.217\pm0.272$ pmol/cm$^2$) but it does not actively bind biotin ($0.280\pm0.025$ pmol/cm$^2$).

It appears that available biotin on the surface is especially important. Available biotin levels that are too high for a particular application, for instance, can result in lower biotinylated oligonucleotide binding due to the excess surface biotin binding to all four biotin-binding sites of avidin. By contrast, available biotin levels that are too low can result in less avidin being bound to the surface, and therefore less biotinylated oligonucleotide. The triblock self-assembly allows good optimization and stabilization of the avidin coupling to provide a specified amount of biotin. This cannot be obtained easily with either photoreactive surfaces alone since the protein denatures or self-assembly alone since the protein and self-assembled coating can be easily washed off. By using a self-assembling molecule on a photosurface it is possible to create a good surface for biosensors and other applications.

Example 6

Using SAMs on a Photosurface to Create an Oligonucleotide Microarray of 4 Analytes By using functionalized self-assembled monolayers covalently bonded to a photosurface highly sophisticated biosensors can be created. The self-assembly approach simplifies the surface manufacture and the block copolymers used provide a good environment for stabilizing biomolecules. Applicants have used the biotinylated SAM-photosurface described above to create a "gene chip" by printing biotinylated oligonucleotides on it, after it was further derivatized by coupling with avidin.

Figure 11:
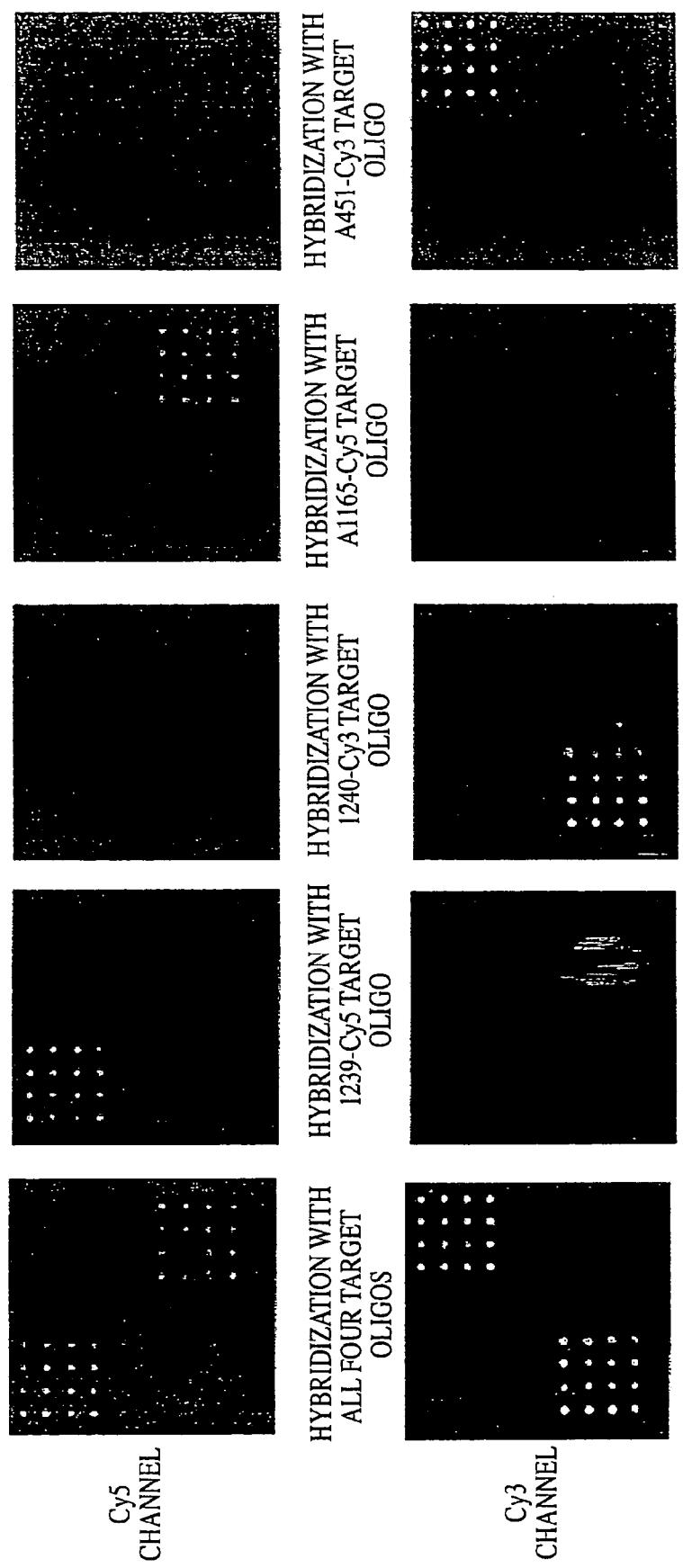
FIG. 11 illustrates the detection of target oligonucleotides by a four analyte oligonucleotide microarray.

Four oligonucleotides were printed in a pattern of four series of 4×4 spots, each with a different capture oligonucleotides as seen in FIG. 11. Oligos are printed at 8 nmol/ml in 150 mM phosphate buffer (pH 7). Once printed and washed a solution of d-biotin (0.1 mg/ml) in 1×PBS buffer with 0.05% Tween-20, the slides are incubated in a solution of d-biotin (0.1 mg/ml) in 5× saline-sodium citrate buffer (SSC)/1-sarcosine (0.1% w/v) at 50° C. for 30 minutes to passivate the remaining avidin on the surface. The slides are re-washed with deionized water and hybridized in a solution of 4×SSC/1-sarcosine (0.1%)/tRNA (2 mg/ml)/d-Biotin (0.1 mg/ml)/detection probe(s) (20 pmol/ml) for 2 hours at 50° C. After hybridization the slides are rinsed with SSC solutions of decreasing molarity and dried. The fluorescent target oligonucleotides are detected on a General Scanning ScanArray 3000 fluorescent scanner with a laser power of 80%, PMT voltage 80%. Hybridizations using multiple analytes were performed on the applicants' avidin surface. The applicants can readily detect at least four analytes in the same assay.

Using these systems the applicants were able to detect each target oligo. The printing conditions were better defined using an oligonucleotide that was both biotinylated and fluorescently labeled (Cy3) allowing for direct detection. This was very useful in determining a dose response curve for printing concentrations and also the uniformity of oligo binding capacity. The average fluorescent signal after printing using the uniformity assay was $22214\pm1911$ with a background of $40\pm6$ and a spot size of 303 µm$\pm$52 using the large pin. This gives an average variation of less than 10% from spot to spot.

Spot size is directly related to the size of the pin used to print. The large pin (syringe tip inner diameter 0.006 inches) creates spot ranging from 300-500 µm averaging approximately 450. The small pin (Telechem International CMP2B) creates spots ranging from 160-180 µm. Overall, the pSil-Avidin chip surface stands up well against comparison with commercial gene chip surfaces. It performs well in hybridization assays giving a signal to noise of >400 for multi-analyte systems.

As seen in the previous example, the use of self-assembling molecules covalently bound by a photosurface was crucial in the construction of this biosensor. The SAM provided not only a good surface with low background signal, but allowed the simple fabrication of the subsequent patterned biomolecules. The base layer of photosurface allows a multitude of different SAMs to be covalently bonded to the underlying substrate, forming a good foundation for the biosensor.

What is claimed is:

1. A coated medical device comprising a medical device including one or more surfaces coated with a coating formed from a composition including self-assembling monolayer molecules covalently adjoined to the one or more surfaces via activation of one or more latent reactive groups.

2. The medical device according to claim 1 wherein the self-assembling monolayer molecules comprise amphiphilic molecules comprised of either: a) a hydrophobic domain which spontaneously associates with the surface from a polar solvent, and of a hydrophilic domain which allows the molecules to be dispersed in the polar solvent and which remains associated with the polar phase after monolayer formation on the surface, or b) a hydrophilic domain which spontaneously associates with the surface from a nonpolar solvent, and of a hydrophobic domain which allows the molecules to be dispersed in a nonpolar solvent and which remains associated with the nonpolar phase after monolayer formation on the surface.

3. The medical device according to claim 1 wherein the self-assembling monolayer is adapted for use with substantially flat or molded surfaces.

4. The medical device according to claim 3 wherein the one or more surfaces of the medical device are provided by a material selected from ceramics, metals and polymeric materials.

5. The medical device according to claim 3 wherein the one or more surfaces of the medical device are provided by a material selected from organosilane-pretreated glasses, organosilane-pretreated silicon materials, and silicon hydrides.

6. The medical device according to claim 3 wherein the material comprises a polymeric material selected from the group consisting of polystyrene, polycarbonate, polyester, polyethylene, polyethylene terephthalate (PET), polyglycolic acid (PGA), polyolefin, poly-(p-phenyleneterephthalamide), polyphosphazene, polypropylene, polytetrafluoroethylene, polyurethane, polyvinyl chloride, polyacrylate (including polymethacrylate), and silicone elastomers, as well as copolymers and combinations thereof.

7. The medical device according to claim 1 wherein the medical device comprises an implantable biosensor.

8. The medical device according to claim 1 wherein the medical device is an implantable device having small pores.

9. The medical device according to claim 8 wherein the medical device comprises a distal protection device for use in various vascular surgical procedures.

10. The medical device according to claim 1 wherein the latent reactive groups comprise photoreactive groups in the form of photoreactive aryl ketones.

11. The medical device according to claim 1 wherein the self-assembling monolayer molecules themselves provide thermochemical reactive groups and wherein binding molecules are attached to the monolayer by reaction between corresponding reactive groups of the binding molecules and the reactive groups of the self-assembling monolayer molecules.

12. The medical device according to claim 11 wherein the binding molecules have one or more corresponding thermochemical reactive groups attached to the self-assembling monolayer molecules via thermochemical interactions between their respective thermochemical reactive groups, and wherein the surface is coated with the monolayer in order to provide an immobilized self-assembling monolayer having the binding molecules attached thereto.

13. The medical device according to claim 12 wherein the binding molecule is selected from the group consisting of coupling molecules and biological polymers, and the binding molecules are attached to the self-assembling monolayer molecules prior to coating and immobilizing the self-assembling monolayer.

14. The medical device according to claim 1 wherein the molecules are selected from the group consisting of linoleamide poly(ethylene glycol) and polyethers.

15. The medical device of claim 1, wherein the medical device is implanted into a body to provide a passivating effect.

16. The medical device of claim 1 wherein the latent reactive groups are provided by the surface itself.

17. The medical device of claim 16 wherein the self-assembling monolayer forming molecules have themselves been provided with latent reactive groups.

18. A coated medical device comprising a medical device including a surface coated with a self-assembling monolayer, the self-assembling monolayer formed by the steps of: a) providing on the surface both latent reactive groups and a monolayer formed of self-assembling monolayer molecules, and b) activating the latent reactive groups under conditions suitable to covalently attach the self-assembled monolayer to the surface and to form a stable monolayer film on the surface, by initiating polymerization of suitable groups provided by self-assembling monolayer molecules and/or by forming intermolecular bonds between the self-assembling monolayer molecules.

19. The medical device of claim 18 wherein the latent reactive groups are provided by the surface itself.

20. The medical device of claim 18 wherein the self-assembling monolayer forming molecules have themselves been provided with latent reactive groups.

21. The medical device of claim 18 wherein the self-assembling monolayer molecules are amphiphilic molecules comprising a plurality of hydrophobic and hydrophilic domains.

22. The medical device of claim 21 wherein the hydrophilic domain comprises a polyether.

23. The medical device of claim 21 wherein the hydrophobic domain comprises poly (propylene oxide), poly (butylene oxide), or a fatty acid.

* * * * *